United States Patent
Calias et al.

(10) Patent No.: US 7,456,220 B2
(45) Date of Patent: Nov. 25, 2008

(54) IMMUNODULATORY COMPOSITIONS AND METHODS OF USE THEREOF

(75) Inventors: Pericles Calias, Melrose, MA (US); Robert J. Miller, Halifax, MA (US); Andrew B. Onderdonk, Westwood, MA (US); Arthur O. Tzianabos, Reading, MA (US)

(73) Assignees: Genzyme Corporation, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 146 days.

(21) Appl. No.: 11/176,701

(22) Filed: Jul. 7, 2005

(65) Prior Publication Data
US 2006/0029662 A1 Feb. 9, 2006

Related U.S. Application Data

(62) Division of application No. 09/543,489, filed on Apr. 6, 2000, now abandoned.

(60) Provisional application No. 60/188,442, filed on Mar. 10, 2000, provisional application No. 60/128,177, filed on Apr. 6, 1999.

(51) Int. Cl.
*A61K 31/17* (2006.01)
(52) U.S. Cl. ..................... 514/588; 514/825
(58) Field of Classification Search .............. 514/588
See application file for complete search history.

(56) References Cited

U.S. PATENT DOCUMENTS

| 4,141,973 | A | 2/1979 | Balazs |
| 4,582,865 | A | 4/1986 | Balazs et al. |
| 4,808,576 | A | 2/1989 | Schultz et al. |
| 4,937,270 | A | 6/1990 | Hamilton et al. |
| 5,057,503 | A | 10/1991 | Czop et al. |
| 5,080,893 | A | 1/1992 | Goldberg et al. |
| 5,288,503 | A | 2/1994 | Wood et al. |
| 5,506,151 | A | 4/1996 | Ito et al. |
| 5,527,893 | A | 6/1996 | Burns et al. |
| 5,679,654 | A | 10/1997 | Tzianabos et al. |
| 5,700,787 | A | 12/1997 | Tzianabos et al. |
| 5,760,200 | A | 6/1998 | Miller et al. |
| 5,801,170 | A | 9/1998 | Gaster et al. |
| 5,817,643 | A | 10/1998 | Jamas et al. |
| 5,849,794 | A | 12/1998 | Bianchi et al. |
| 5,965,566 | A | 10/1999 | Greenwald et al. |

FOREIGN PATENT DOCUMENTS

| WO | WO 95/09619 | 4/1995 |
| WO | WO 99/06354 | 2/1999 |

OTHER PUBLICATIONS

Onderdonk, A.B. et al., "Anti-Infective Effect of Poly-β1-6-Glucotriosyl-β1-3-Glucopyranose Glucan In Vivo," *Infection and Immunity*, 60(4):1642-1647 (1992).

Tzianabos, A.O. et al., "Protection Against Experimental Intraabdominal Sepsis by Two Polysaccharide Immunomodulators," *Journal of Infectious Diseases*, 178:200-206 (1998).

Tzianabos, A.O. et al., "Polysaccharide-mediated Protection Against Abscess Formation in Experimental Intra-Abdominal Sepsis," *Journal of Clinical Investigation*, 96(6):2727-2731 (1995).

Kuo, J.W. et al., "Chemical Modification of Hyaluronic Acid by Carbodiimides," *Bioconjugate Chem.*, 2:232-241 (1991).

Beuvery et al., Analytical, Toxicological and Immunological Consequences of hte Use of N-Ethyl-N'-(3-Dimethylaminopropyl) Carbodiimide as Coupling Reagent for the Preparation of Meningococcal Group C Polysaccharide-Tetanus Toxoid 1986.

*Primary Examiner*—Barbara P Badio
(74) *Attorney, Agent, or Firm*—Hamilton, Brook, Smith & Reynolds, P.C.

(57) ABSTRACT

The invention relates to immunomodulatory compositions and related methods. The immunomodulatory compositions of a formula disclosed herein are useful for the prevention of sepsis and the treatment and prevention of diseases associated with inflammation and/or NOS.

1 Claim, 4 Drawing Sheets

IMMUNODULATORY COMPOSITIONS AND METHODS OF USE THEREOF

RELATED APPLICATION

This application is a divisional of U.S. application Ser. No. 09/543,489, filed Apr. 6, 2000, now abandoned which claims the benefit of U.S. Provisional Application Nos. 60/188,442, filed Mar. 10, 2000 and 60/128,177 filed Apr. 6, 1999. The entire teachings of these applications are incorporated herein by reference.

FIELD OF THE INVENTION

The invention relates to immunomodulators and methods for modulating an immune response. In particular, the invention relates to methods, and related products, for preventing an inflammatory response, methods for preventing or inhibiting the onset of sepsis, surgical adhesions, inflammatory disorders, and restenosis.

BACKGROUND OF THE INVENTION

An inflammatory response is an important element of a host's natural defense mechanism against pathogens and is also involved in wound healing. Despite the beneficial role that the inflammatory response plays in host survival, excessive inflammation may have clinically adverse results in some medical conditions. Sepsis is a disorder arising from infection that results in an excessive inflammatory response.

Intra-abdominal sepsis is often caused by leakage of microorganisms, in particular a specific type of bacteria, from the intestine into the peritoneal cavity. This leakage typically results from complications associated with abdominal surgery, such as the perforation of the large bowel and abdomen, complications subsequent to abdominal surgery, or bowel disease. Numerous clinical and experimental studies have shown that the release of the colonic contents into the peritoneal cavity can lead to wide-spread septicemia.

Traditional approaches for preventing sepsis have involved the use of antibiotics and antimicrobial agents with activity against both the facultative and obligate anaerobic components of the intestinal flora, and particularly against Gram-negative bacteria such as E. coli. However, even with the use of antibiotics, that have had some impact on the infection rate associated with intra-abdominal sepsis, the infection rate is still about 15% for all abdominal surgeries, and 30% for high-risk gastrointestinal surgeries. Since there are in excess of 1.5 million abdominal surgeries performed in the United States every year, and perhaps another 1.5 million surgeries world-wide, the risk of sepsis represents a significant medical problem.

It will be appreciated that there is a need for a pharmaceutical preparation which is capable of protecting a host organism against sepsis and other inflammatory disorders.

SUMMARY OF THE INVENTION

The invention relates to immunomodulating methods and related products and compositions. The compositions of the invention are useful for preventing inflammatory responses and/or preventing infection in a subject which might result in an excessive inflammatory response, such as sepsis. It was discovered according to the invention that derivatives of urea were capable of preventing undesirable inflammatory responses, such as those arising from infection, autoimmune disease, etc. It was discovered surprisingly, according to the invention, that the pharmaceutical compositions described herein when administered to a subject prevented a pro-inflammatory response, which ordinarily would occur, and which ordinarily would lead to tissue damage and possibly mortality. The pharmaceutical compositions are also useful for preventing infection, as well as surgical adhesion formation.

The invention in one aspect is a composition. The composition includes a pharmaceutical preparation of a compound having the following formula:

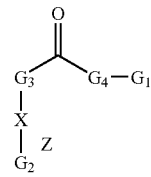

wherein G1 is selected from the group consisting of $(C_1-C_6)$ alkyl, $(C_1-C_6)$ alkenyl, aryl group or a heteroaryl group, wherein the aryl or heteroaryl is a ring having 5, 6, or 7 atoms, and wherein at least one atom of the heteroaryl is selected from the group consisting of a sulfur, a nitrogen, and an oxygen atom, wherein G2 is a group having a net charge, preferably a net positive charge selected from the following: —CN $(R_1R_2R_3)$, —N—$(R_1R_2R_3)$, or a heteroaryl group, wherein the heteroaryl is a ring having 5, 6, or 7 atoms, and wherein at least one atom of the heteroaryl is selected from the group consisting of a sulfur, a nitrogen, and an oxygen atom, wherein $R_1$, $R_2$, and $R_3$ independent of one another are selected from the group consisting of —H, —$CH_3$, —$CH_2CH_3$, or other linear alkyl groups such as propyl, butyl, or pentyl; wherein G3 and G4 independent of one another are selected from the group consisting of N, S, O, $(C_1-C_6)$ alkyl, and $(C_1-C_6)$ alkenyl, wherein X is a $(C_1-C_{12})$ alkyl, and wherein Z is a charged species, the charge depends on the charge of G2, and thus preferably is a net negative charge, in a pharmaceutically acceptable carrier.

In some embodiments the compound has the following formula:

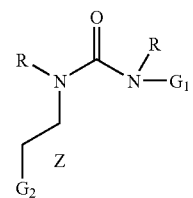

wherein each R is independently selected from the group consisting of hydrogen, $(C_1-C_6)$ alkyl, and $(C_1-C_6)$ alkenyl.

In preferred embodiments the compound is N-ethyl-N'-(3-dimethylaminopropyl) urea or N-ethyl-N'-(3-dimethylaminopropyl) urea methiodide. In other embodiments the compound is 5-50% by weight of the composition. In yet other embodiments the pharmaceutically acceptable carrier is a buffer such as a succinate, phosphate buffer or simply a solution of NaCl.

The pharmaceutical compositions of the invention optionally may also include another therapeutic compound. Other therapeutic compounds include but are not limited to anti-infectious disease agents, such as antibacterial agents, antiviral agents, and anti-fungal agents and anti-inflammatory agents.

In a further aspect, the invention is a prodrug of N-ethyl-N'-(3-dimethylaminopropyl) urea or N-ethyl-N'-(3-dimethylaminopropyl) urea methiodide.

Suitable prodrugs include gels formed from an activated polyanionic polysaccharide. Typical polyanionic polysaccharides include hyaluronic acid, and carboxymethylcellulose, or a combination of hyaluronic acid and carboxymethylcellulose. The activated polyanionic polysaccharide can be a derivatized polyanionic polysaccharide or a cross-linked polyanionic polysaccharide.

In one embodiment, the activated polyanionic polysaccharide can be prepared by reacting the polyanionic polysaccharide with a derivatizing agent in an aqueous medium under suitable reaction conditions. The preferred derivatizing agent is a carbodiimide. The preferred pH for carrying out the reaction is from about 3.5 to about 8.0, and more preferably 4.0 to 5.1. The preferred concentration of the polyanionic polysaccharide in the pharmaceutical preparation is from about 0.01% by weight to about 4% by weight, and more preferably from about 0.1% by weight to about 2.5% by weight. The molar ratio of moles of carbodiimide to moles of carboxyl groups of polyanionic polysaccharide is preferably in the range of about 0.5:1 to 2:1, and the molecular weight of the polyanionic polysaccharide is typically in the range of 25,000 daltons to 2 million daltons. The preferred carbodiimide is 1-ethyl-3-(3-dimethylaminopropyl) carbodiimide or 1-ethyl-3-(3-dimethylaminopropyl) carbodiimide methiodide. Methods for preparing derivatized polyanionic polysaccharides of this type are more fully described in U.S. Pat. No. 5,017,229.

In another embodiment, the activated polyanionic polysaccharide can be prepared by reacting the polyanionic polysaccharide with a cross-linking agent in an aqueous medium.

In other aspects the composition of the invention is in a sustained release formulation and the composition is formulated to release the compound over a period of at least 2 hours. In other embodiments it is formulated to release the compound over a period of at least 12 hours, at least 24 hours, at least 2 days, or at least 7 days.

The sustained release formulation is a device that releases the compound over an extended period of time and includes in some embodiments a sustained release capsule, a fatty acid carrier, preferably a fatty acid carrier includes $C_9$-$C_{20}$ fatty acids, a microparticle or microencapsulated product, bioadhesive polymers, or a medicinal pump.

A method for preventing an inflammatory response is provided according to other aspects of the invention. The method involves administering to a subject an effective amount of a pharmaceutical composition of the invention to prevent an inflammatory response. In preferred embodiments the pharmaceutical composition is administered to the subject over a period of time.

In some embodiments the pharmaceutical composition is administered to the subject between 2 and 48 hours before exposure of the subject to the infectious agent and in other embodiments the pharmaceutical composition is administered to the subject between 2 and 8 hours before exposure of the subject to the infectious agent.

The subject is any subject susceptible to a disorder having an inflammatory component. For instance the subject may be at risk of exposure to an infectious agent or at risk of developing sepsis.

In some embodiments the inflammatory disease is selected from the group consisting of meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants, multiple sclerosis, chronic inflammatory disease, and inflammatory bowel disease.

In another aspect the invention is a method for preventing disorders associated with nitric oxide synthase (NOS). The method includes administering to a subject an effective amount of a pharmaceutical composition of the invention to prevent nitric oxide synthase (NOS) activity. This enzyme synthesizes NO from arginine.

In one embodiment the pharmaceutical composition is administered to the subject over a period of time. In another embodiment the subject has or is at risk of developing a disease selected from the group consisting of Hypertension, Familial Hyperchloesterolemia, Endothelial Dysfunction, Atherosclerosis, Graft/Transplantation Rejection, Asthma, Neurogenic Airway Edema, Ulcerative Colitis, Colonic Inflammation, Periodontal Disease, Cystic Fibrosis, Diabetes Melitis, Vascular Hyporeactivity, Cerebral Ischemia, Migraine, Alzheimer's Disease, and Multiple Sclerosis.

The invention in another aspect is a method for preventing surgical adhesions. The method involves administering to a subject an effective amount of a pharmaceutical composition of the invention to prevent surgical adhesions. In preferred embodiments the pharmaceutical composition is administered to the subject over a period of time. In other embodiments the pharmaceutical composition is administered to the subject at the same time as surgery.

In some embodiments the pharmaceutical composition is administered to the subject between 2 and 48 hours before surgery and in other embodiments the pharmaceutical composition is administered to the subject between 2 and 8 hours before surgery.

The pharmaceutical compositions of the invention can be delivered by any route known in the art. For instance the pharmaceutical composition may be administered systemically, e.g., orally, parenterally or may be administered locally. In one embodiment they are delivered in a sustained release device.

The surgery may be any type of surgery, where there is a risk of surgical adhesions associated with the surgery. In some preferred embodiments the subject is undergoing a surgery selected from the group consisting of abdominal surgery, gynecological surgery and cardiac surgery.

According to another aspect the invention is a method of inhibiting restenosis. The method involves the administration of the compounds of the invention in an effective amount to prevent proliferation of cells contributing to the restenosis.

In a preferred embodiment the restenosis is arterial restenosis of the arterial wall caused by the proliferation of endothelial and/or vascular smooth muscle cells on the area of trauma after balloon angioplasty.

In another aspect the invention relates to a method for treating an IL-10 associated disorder.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 4 is a bar-graph depicting IL-10 production after sublethal injection of *E. coli* in saline or HA/CMC gel treated animals.

DETAILED DESCRIPTION

Figure 1:
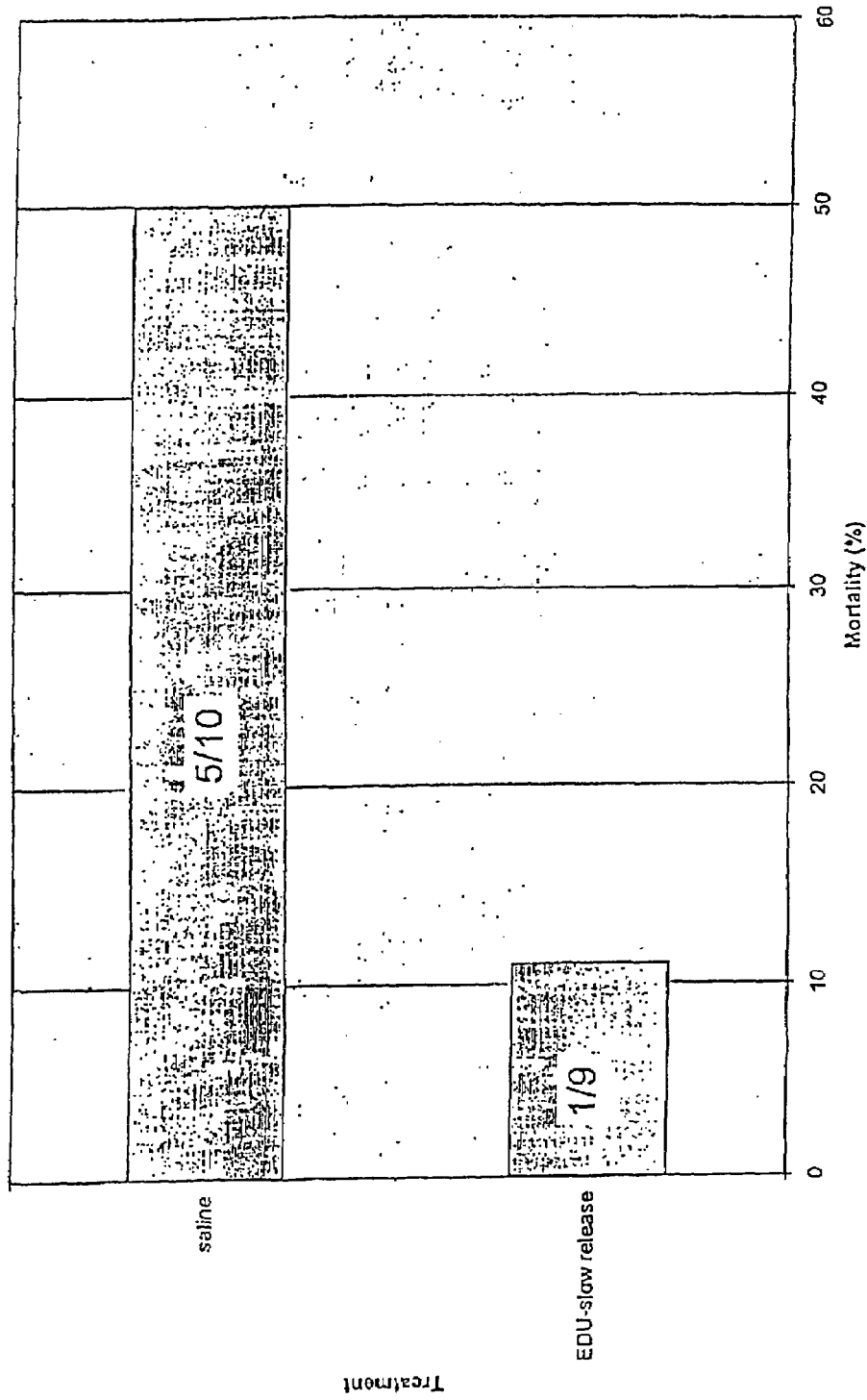
FIG. 1 is a bar graph depicting the effect of N-ethyl-N'-(3-dimethylaminopropyl) urea (EDU) on mortality in a rat model of sepsis. Rats were treated with saline or EDU in a slow release format and challenged with cecal contents.

It has been discovered according to the invention that pharmaceutical compositions described herein are useful for preventing inflammation or infection in a subject, such as a bacterial infection which may result in sepsis, as well as preventing adhesion formation and restenosis.

The composition includes a pharmaceutical preparation of a compound having the following formula:

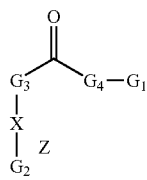

wherein G1 is selected from the group consisting of $(C_1-C_6)$ alkyl, $(C_1-C_6)$ alkenyl, aryl group or a heteroaryl group, wherein the aryl or heteroaryl is a ring having 5, 6, or 7 atoms, and wherein at least one atom of the heteroaryl is selected from the group consisting of a sulfur, a nitrogen, and an oxygen atom, wherein G2 is a group having a net charge, preferably a net positive charge selected from the following: —CN($R_1R_2R_3$), —N—($R_1R_2R_3$), or a heteroaryl group, wherein the heteroaryl is a ring having 5, 6, or 7 atoms, and wherein at least one atom of the heteroaryl is selected from the group consisting of a sulfur, a nitrogen, and an oxygen atom, wherein $R_1$, $R_2$ and $R_3$ independent of one another are selected from the group consisting of —H, —CH$_3$, —CH$_2$CH$_3$, or other linear alkyl groups such as propyl, butyl, or pentyl, wherein G3 and G4 independent of one another are selected from the group consisting of N, S, O, $(C_1-C_6)$ alkyl, and $(C_1-C_6)$ alkenyl, wherein X is a $(C_1-C_{12})$ alkyl, and wherein Z is a charged species, the charge depends on the charge of G2, and thus preferably is a net negative charge, in a pharmaceutically acceptable carrier. N-ethyl-N'-(3-dimethylaminopropyl) urea (EDU) and N-ethyl-N'-(3-dimethylaminopropyl) urea methiodide are preferred compounds of the invention.

In some embodiments the compound has the following formula:

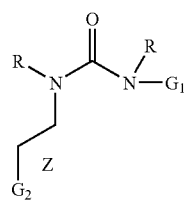

wherein each R is independently selected from the group consisting of hydrogen, $(C_1-C_6)$ alkyl, and $(C_1-C_6)$ alkenyl.

N-ethyl-N'-(3-dimethylaminopropyl) urea (EDU) and N-ethyl-N'-(3-dimethylaminopropyl) urea methiodide can be prepared by a variety of techniques which are well known in the prior art. These compounds can be prepared by the reaction of an isocyanate with an amine, or by the aminolysis of bis (4-nitrophenyl) carbonate as described in Izdebski, et al., *Synthesis*, p. 423-425 (1989). See, also, R. Timkovich, *Analytical Biochemistry*, v. 79, p. 135-143 (1977). The conversion of the corresponding carbodiimides, N-ethyl-N'-(3-dimethylaminopropyl) carbodiimide (EDC) and N-ethyl-N'-(3-dimethylaminopropyl) carbodiimide methiodide, to the respective ureas can be accomplished by reaction of acidic acid in methylene chloride, or by hydrolysis, as disclosed in Sheehan, et al., *J. Org. Chem.* p. 2525-2528 (1961), and as illustrated by the following reaction scheme:

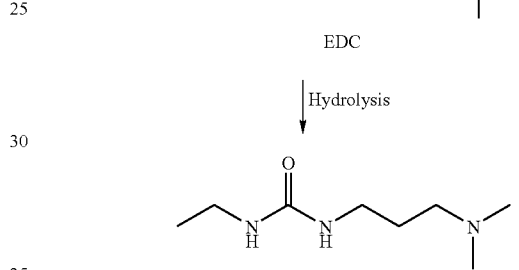

The following compounds are exemplary species of the preferred compounds:

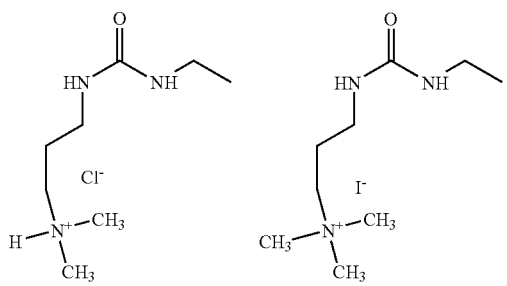

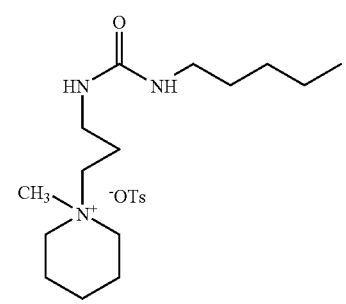

-continued
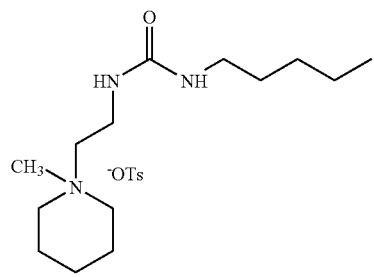
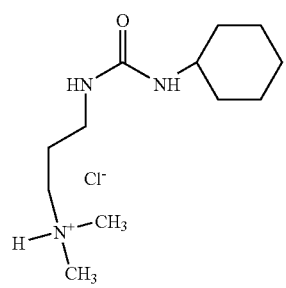
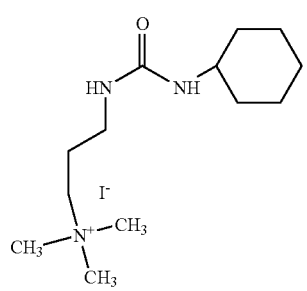
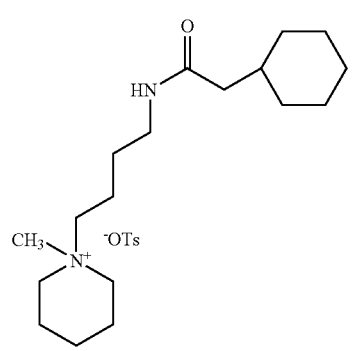
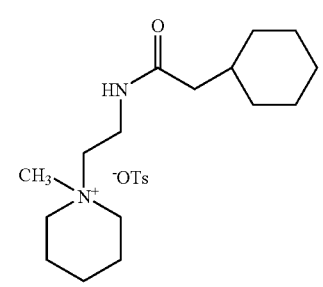
-continued
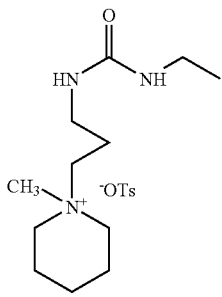
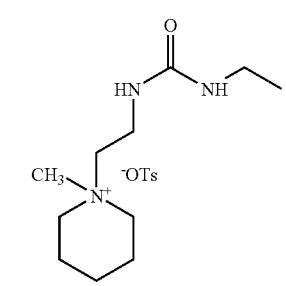
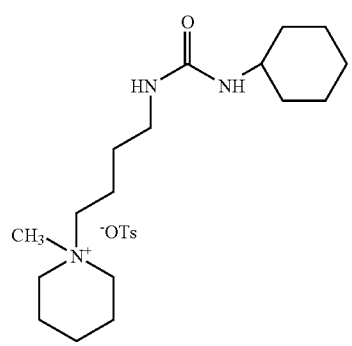
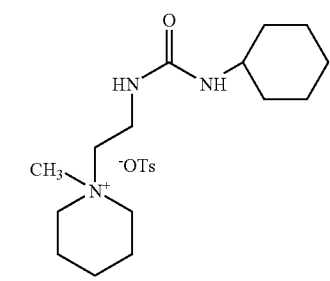
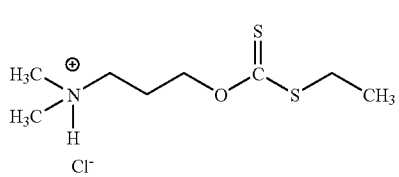

-continued
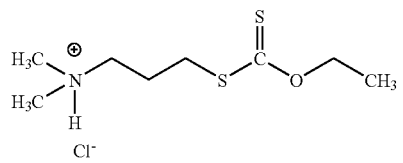
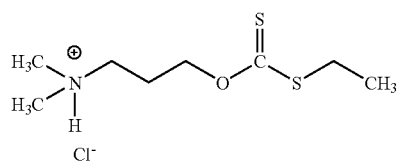
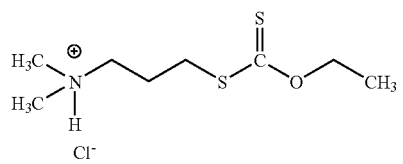
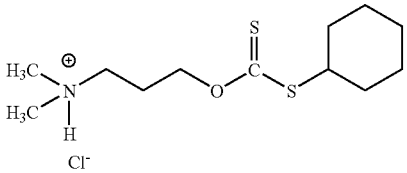
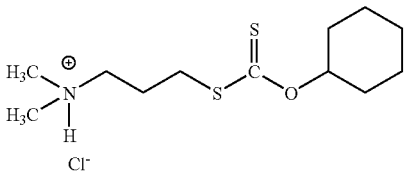
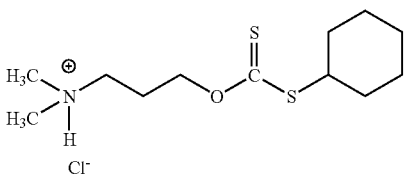
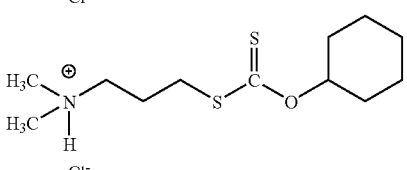
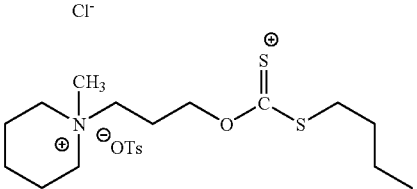
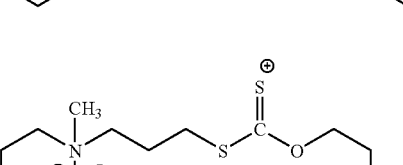
-continued
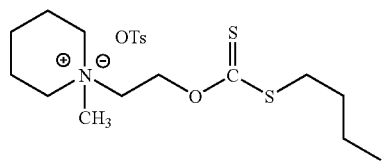
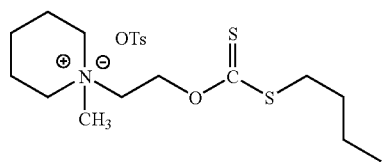
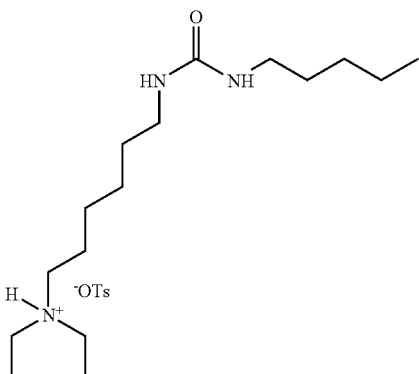
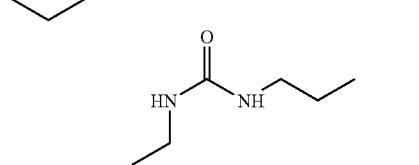
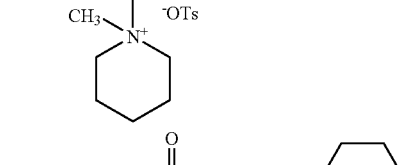
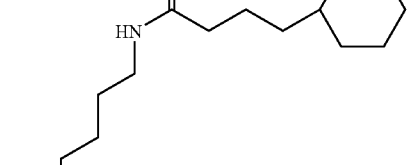
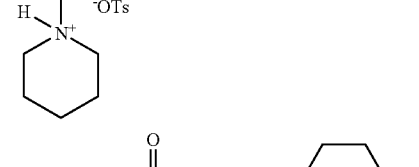
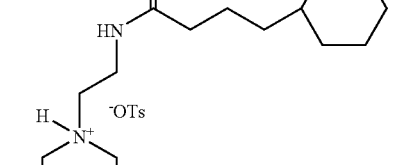

-continued

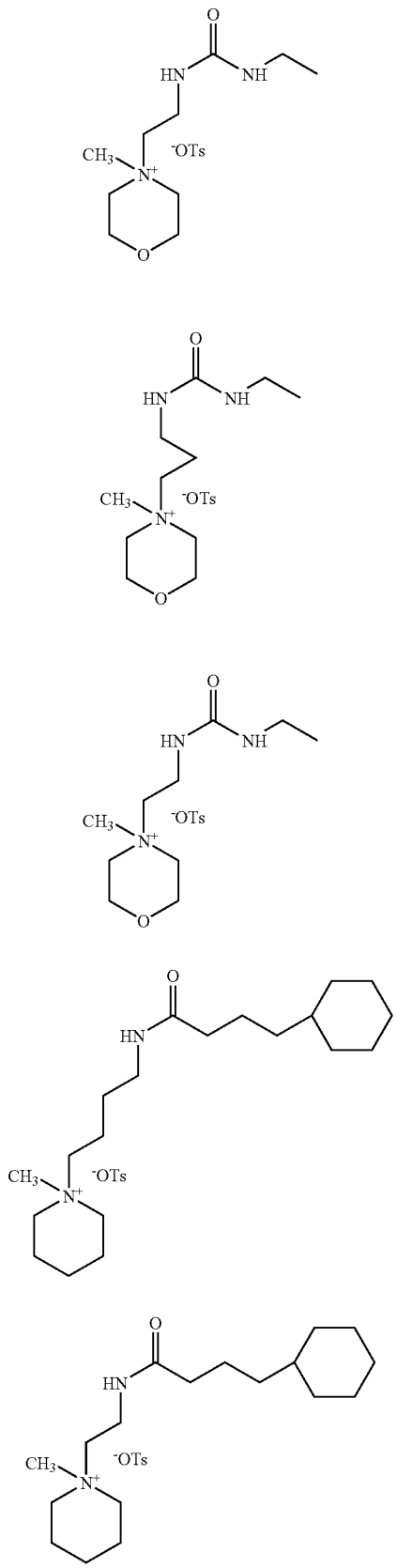

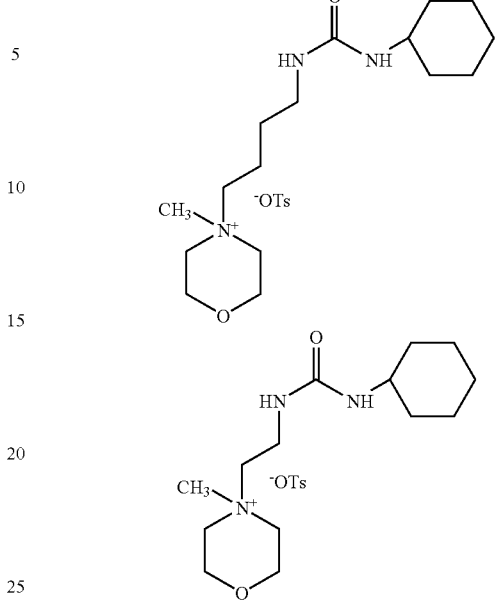

Surprisingly, EDU has now been found to have biological activity even though this compound has previously been thought to be relatively inactive. See, for instance, Beuvery, et al., *IABS/WHO/UCSF Symposium on Use and Standardization of Chemically-Defined Antigens*, v. 63, p. 117-128 (1986).

N-acylurea modified, or "derivatized", polyanionic polysaccharides, which are prepared by the reaction of a carbodiimide with a polyanionic polysaccharide, have also been found to act as prodrugs for the delivery of EDU into the body of a subject. When the derivatized polyanionic polysaccharide is administered to the subject, it is at least partially converted to EDU by hydrolysis and released in the subject. The polyanionic polysaccharide thereby acts, in effect, like a drug delivery vehicle or carrier for EDU.

As used herein, and unless otherwise indicated, the term "polyanionic polysaccharide" denotes a polysaccharide containing more than one negatively charged group, e.g., carboxyl groups at pH values above about 4.0. This includes hyaluronic acid ("HA"), any of its hyaluronate salts, including, for example, sodium hyaluronate (the sodium salt), potassium hyaluronate, magnesium hyaluronate, and calcium hyaluronate, carboxymethylcellulose ("CMC"), and mixtures of hyaluronic acid and carboxymethylcellulose ("HACMC").

The term "pharmaceutically acceptable carrier" denotes a carrier substance that potentiates, and does not significantly diminish, the effect of the active agent in the body.

A "biocompatible" substance, as the term may be used herein, is one that has no medically unacceptable toxic or injurious effects on biological function.

An "activated" polyanionic polysaccharide is a polyanionic polysaccharide that has been chemically modified by intermolecular ionic or covalent bonding, such as by derivatizing or cross-linking. The degree of derivatizing or cross-linking is an important feature of the polyanionic gels of this invention, and it can be measured by the amount of cross-linking agent or derivatizing agent consumed in the preparation of the activated product, or the amount of by-product produced in the reaction.

A "derivatizing agent" is a substance that, in a mixture, such as an aqueous, organic or organic/aqueous mixture, including the polyanionic polysaccharide, renders the carboxyl groups on the polyanionic polysaccharide vulnerable to nucleophilic attack.

A "cross-linking agent" is a substance that forms a 3-dimensional network by covalent bonding with adjacent polyanionic polysaccharide molecules, usually by reaction in an aqueous solution at elevated pH levels.

An "acyl derivative," as that term may be used herein, is a compound produced by the displacement of the hydroxyl group bound to the acyl carbon atom of a carboxylic acid moiety by either the reaction of the carboxyl group with a nucleophililc group of another compound, or by the rearrangement of the O-acylisourea group formed by reaction of the carboxyl group with a carbodiimide. Examples of acyl derivatives include acylureas, acylisoureas, amides, thioesters, and phenolates.

A derivatized polyanionic polysaccharide, such as derivatized hyaluronic acid, can be prepared by reacting the hyaluronic acid with a suitable derivatizing agent, such as a carbodiimide, in the presence or absence of a nucleophile. The resulting product may be water soluble or relatively water insoluble, depending on the reaction conditions and the relative proportions of ingredients used in the reaction mixture. The reaction of the carbodiimide with the carboxyl group of the hyaluronic acid proceeds through the addition of the free carboxylate to one of the double bonds of the diimide to give the O-acylisourea ("OAU") derivatives of the hyaluronic acid and the carbodiimide. In the presence of a nucleophile, such as a primary amine, the amide derivative of the hyaluronic acid forms as well as the acylurea by the unimolecular O→N rearrangement of the O-acylisourea. In the absence of a nucleophile, the intramolecular rearrangement from the O-acylisourea derivatives to the N-acylurea derivatives is the predominant reaction.

The hyaluronic acid, or a salt of hyaluronic acid, such as sodium hyaluronate, is dissolved in water to make an aqueous mixture. HA from any of a variety of sources can be used. As is well known to those skilled in the art, HA can be extracted from animal tissues or harvested as a product of bacterial fermentation. Hyaluronic acid can be produced in commercial quantities by bioprocess technology, as described for example in PCT Publication No. WO 86/04355. Preferably the initial concentration of HA in this aqueous mixture is in the range of between 0.05% to 2.0% by weight, and more preferably 0.1% to 1% by weight. Subsequent reactions are slower and less effective at significantly lower concentrations, while significantly higher concentrations are difficult to handle owing to their high viscosity. The aqueous HA mixture should be acidic, preferably having a pH between 3.5 and 8.0, more preferably between pH 4.0 and pH 5.1. At lower pH values the preferred activating agent, EDC, is unstable, and at higher values the reaction rate is diminished. Preferably, hydrochloric acid is added to adjust the pH, although other known acids can be used. The molecular weight of the hyaluronic acid is advantageously in the range of from about 25,000 daltons to about 2,000,000 daltons.

Once the pH of the aqueous HA mixture has been adjusted, a carbodiimide is admixed with the HA. Preferred carbodiimides include EDC (1-ethyl-3-(3-dimethylaminopropyl) carbodiimide or ETC (1-ethyl-3-(3-dimethylaminopropyl)) carbodiimide methiodide. EDC is soluble in water and is preferred.

The sequence and mode of addition of the reagents are not critical factors, but the ratio of the carbodiimide to HA is important. Best results are obtained when the ratio of carbodiimide to HA ranges from about 0.5:1 to 2:1. Lower ratios typically form more soluble products, while higher ratios typically result in soluble products.

In one embodiment, the derivatized HA/CMC gels of this invention are prepared by the reaction scheme shown below. As shown, HA/CMC is reacted with a derivatizing agent, such as the carbodiimide EDC, in the absence of a nucleophile.

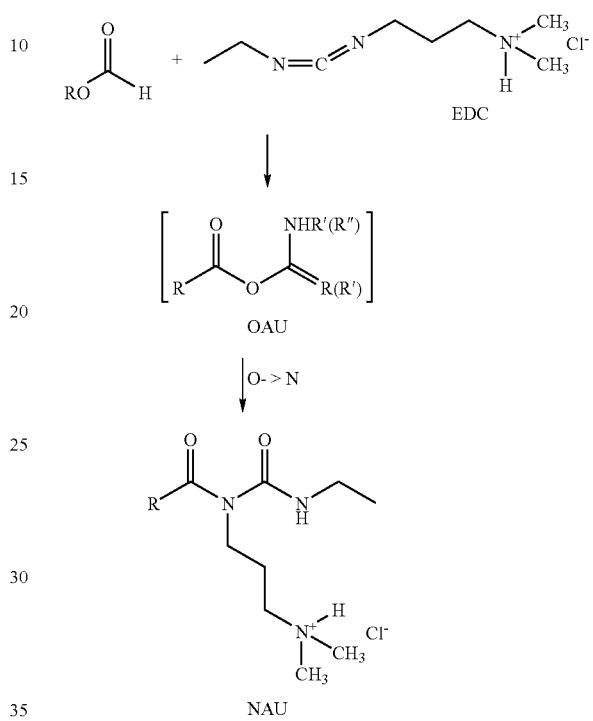

wherein R is HA or CMC, R' is Ethyl, and R" is

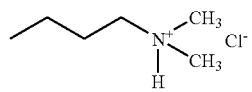

Normal reaction conditions can result in a 5% to 20% (molar basis) modification of the carboxyl groups on each polymer molecule. The carboxyl groups are both protonated and deprotonated, while the NAU modified groups are positively charged.

An exemplary diimide modified hyaluronic acid molecule is shown below:

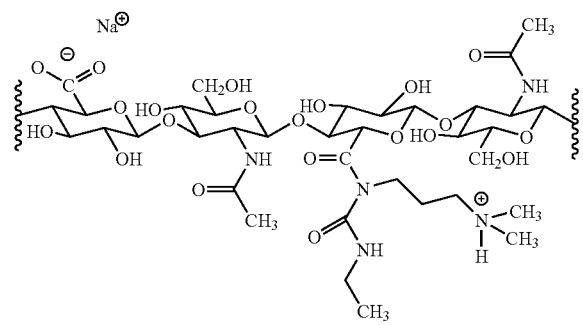

An exemplary diimide modified carboxymethylcellulose molecule is shown below:

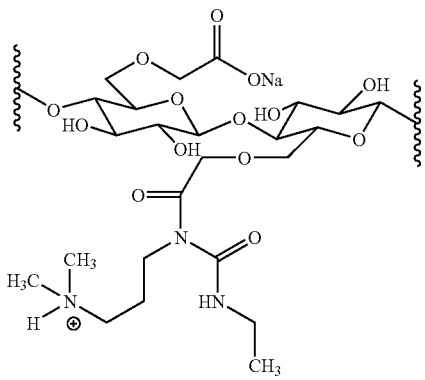

The reaction product is a dried powder which can be dispersed in a buffered solution or physiological saline at concentrations of between 1% and 6% by weight. The product is capable of being terminally sterilized, which facilitates its storage and handling.

One particularly useful derivatized gel product is SEPRA-GEL®, a proprietary hyaluronic acid/carboxymethylcellulose gel product available from the Genzyme Corporation.

While not intending to be bound by any particular theory or mechanism, it is believed that the immunomodulating pharmaceutical compositions of the invention function in some aspects by inducing levels of IL-10. IL-10 is an anti-inflammatory cytokine that causes the down-regulation or inhibition of pro-inflammatory factors, cytokines, or cells. When the body encounters an inflammatory stimulus such as that which occurs with intra-abdominal infections, the elicitation of pro-inflammatory cytokines such as TNF-α is followed by the release of anti-inflammatory cytokines such as IL-10. IL-10 serves to dampen or mitigate the inflammatory process in order to maintain homeostasis and prevent excessive inflammation. In this manner, the invention provides methods for protecting against sepsis, adhesion formation, or excessive inflammation by the administration of each of these materials. It has also been discovered according to the invention that the immunomodulating pharmaceutical compositions of the invention function to prevent nitric oxide synthase (NOS) activity.

The anti-inflammatory effects of the compositions of the invention are particularly effective when the pharmaceutical composition is administered to the subject over a period of time. For instance, when the pharmaceutical compositions are slowly released from a sustained release vehicle, a consistent and effective anti-inflammatory response is achieved.

As demonstrated in the Examples below when EDU is administered in an animal model of intra-abdominal sepsis, EDU significantly inhibits mortality. The results of the study are shown in FIG. 1. Only one of the 9 animals treated with EDU died (10% mortality), whereas 5 out of 10 of the animals that were administered saline died (50% mortality).

The pharmaceutical compositions of the invention are useful for preventing inflammatory responses, protecting against adhesions arising from surgery, preventing against sepsis, preventing restenosis, and preventing other diseases having an inflammatory component and diseases associated with NOS activity.

The terms "prevent" and "preventing" as used herein refer to inhibiting completely or partially a biological response, as well as, inhibiting an increase in a biological response. For instance, prevention of an inflammatory response refers to the partially or completely inhibiting an inflammatory response, as well as, inhibiting an increase in an inflammatory response. Thus the term prevention embraces the use of the compounds for inhibiting an inflammatory response before it begins or treating a subject in which inflammation has already begun in order to slow the progression or inhibit altogether the inflammation. Likewise, prevention of adhesion formation or NOS activity refers to partially or completely inhibiting adhesion formation or NOS activity respectively, as well as, inhibiting an increase in adhesion formation or NOS activity respectively. The term prevent when used with respect to prevention of restenosis refers to partially or completely inhibiting cellular proliferation that causes restenosis, as well as, inhibiting an increase in cellular proliferation associated with restenosis.

An inflammatory response refers to the induction of at least one pro-inflammatory cytokine, factor or cell. Thus the prevention of an inflammatory response refers to the partial or complete inhibition of the induction of at least one pro-inflammatory cytokine, factor or cell or an inhibition of an increase in the levels of at least one pro-inflammatory cytokine, factor or cell. Pro-inflammatory cytokines, factors and cells include but are not limited to Tumor Necrosis Factor-α (TNF-α), Interleukin-1β (IL-1β), Transforming Growth Factor-β (TGF-β), Interleukin-(IL-6), prostaglandins, and Nitric Oxide (NO).

Sepsis is a disorder that arises from an excessive pro-inflammatory response and often results in mortality. Sepsis can develop in response to infection caused by any class of microorganism, but Gram-negative and gram-positive bacteria account for most cases. The pharmaceutical compositions of the invention are useful for treating sepsis because they prevent or reduce the pro-inflammatory response, thus reducing the likelihood of death. Some of the many factors that predispose a subject to the development of Gram-negative bacteria include diabetes mellitus, lymphoproliferative disorders, cirrhosis of the liver, burns, invasive procedures or devices and drugs that cause neutropenia. Factors that predispose a subject to the development of Gram positive bacteria include vascular catheters, indwelling mechanical devices, burns, and intravenous drug injection. In preferred embodiments the compositions of the invention are useful for preventing intra-abdominal sepsis.

In another aspect of the invention, a method is provided for inducing protection against postoperative surgical adhesion formation associated with many common types of surgery. Adhesions are a common complication of surgery that involve abnormal union of tissue surfaces that often occurs during the healing process of injured cells, tissues and organs. Postoperative surgical adhesions are a major complication of abdominal, pelvic, gynecologic, cardiothoracic, orthopedic and neuro-surgeries. Adhesions may result after a trauma sustained by the body such as a surgery or a wound and may develop in a variety of areas in the body. The type and degree of damage caused by adhesions is variable, ranging from life-threatening, as in the intestines due to blockage, to extremely disabling, as in tendons or spinal cord, to chronic pain and infertility in the pelvic cavity, to being obstructive of further surgery in the pericardium. Adhesions that form in relation to intestinal surgery, e.g., bowel resection, hernia repair, etc. may cause obstruction of the intestine. Adhesions that form near a bone fracture site may reduce or hinder the normal movement of the area of repair by restricting the natural movement of tendons over the adjacent bone. Adhesions may also form in the vicinity of nerves and disrupt nerve transmissions with a resultant diminution of sensory or motor function. Postoperative formation of pelvic adhesions remains a serious problem in patients undergoing gynecological surgery and is a principal cause of infertility. In general, the most common causes of pelvic adhesions in women are prior surgery, endometriosis and pelvic inflammatory disease. While the exact mechanism underlying adhesion formation remains unknown, it is believed that the induction of IL-10 is useful in the prevention of surgical adhesion formation.

Traditionally these adhesions have been thought to be caused by a combination of factors including manipulative trauma and drying of the tissues during the surgery itself. A number of techniques attempting to ameliorate these problems have been previously described. Current clinical methods directed toward reducing the formation of postoperative surgical adhesions generally rely on placement of a film or gel directly into the operative site with the intention of creating a physical barrier between surfaces likely to become involved in adhesion formation. These methods remain cumbersome for the surgeon. Highly concentrated solutions of a number of polymers have been used to coat the surgical area before and during surgery so as to minimize the drying and act as cushion to prevent some of the manipulative trauma. Examples of the techniques are described in U.S. Pat. No. 4,819,617 to Goldberg et al. and U.S. Pat. No. 4,886,787 to De Belder et al. Among the materials used are polyvinylpyrrolidone (PVP), dextrans, carboxymethylcelluloses, and a number of other polymers such as protein or polypeptide solutions.

It was discovered according to the invention that administration of the compounds of the invention, locally or systemically are capable of inducing protection against postoperative surgical adhesion formation. The finding is particularly surprising in view of the prior art teaching that local administration of certain polymers into the surgical site to function as a physical barrier is effective for reducing the incidence of postoperative surgical adhesion. Surprisingly, it was discovered according to the invention that the compounds of the invention are effective for preventing adhesion formation even when they are not functioning as a physical barrier.

Thus, the compositions of the invention are useful for treating or preventing adhesions that form in any site and that have potential or actual deleterious effects. These include primary, and especially secondary, adhesions in the following: in the abdominal cavity, including intestine to intestine, and intestine to peritoneum; in the pelvic cavity, including adhesion of the uterus, ovaries or fallopian tubes to other structures including each other and the pelvic wall; in tendons and their support structures, including tendon to pulley or to synovium; in the repair of nerve sheaths; in repair of the spinal column or disks; in the pericardium; in treatment of joints for inflammation and to prevent pannus formation; and in any situation in which adhesions form which impair function or cause pain.

The prevent postoperative surgical adhesion formation in a subject includes prophylactic treatment to prevent adhesion formation following planned surgical procedures as well as following emergency operations. In addition to the surgical procedures described above, elective surgeries include the following intraabdominal surgeries: right hemicolectomy; left hemicolectomy; sigmoid colectomy; subtotal colectomy; total colectomy; laparoscopic or open cholecystectomy; gastrectomy; pancreatectomy; splenectomy; liver, pancreas, small bowel, or kidney transplantation; lysis of adhesions; cesarean sections and other pelvic procedures, uterine surgery, etc. Emergency intraabdominal surgeries include those to correct the following conditions: perforated ulcer (duodenal or gastric); perforated diverticulitis; obstructive diverticulitis; bowel obstruction; perforated appendicitis; blunt abdominal trauma; penetrating abdominal trauma; ruptured abdominal aortic aneurysm, cardiac surgeries, open and endoscopic orthopedic surgeries, neurosurgeries, gynecologic and pelvic surgeries, and surgeries to correct wound infections.

The compounds are administered in an effective amount for inducing protection against postoperative surgical adhesion formation. An effective amount for inducing protection against postoperative surgical adhesion formation as used herein is that amount of an immunomodulating compound of the invention that will, alone or together with further doses or additional therapeutic compounds, inhibit or prevent the formation of postoperative surgical adhesion.

The invention also relates to methods for preventing diseases having an inflammatory component and/or diseases associated with NOS A "disease having an inflammatory component" as used herein refers to any disease or condition characterized by local inflammation at a site of injury, disease, or infection and includes but is not limited to autoimmune diseases, certain forms of infectious inflammatory states, meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants multiple sclerosis, and/or inflammatory bowel disease, e.g., ulcerative colitis. Each of these disorders is associated with inflammation and can be prevented by administering to a subject having one or more of these diseases the pharmaceutical compositions of the invention.

A "disease associated with NOS" as used herein refers to any disease or pathological condition characterized by tissue which is damaged by expression or production of nitric oxide (NO). NOS is an enzyme which catalyzes the production of NO. The compounds of the invention prevent NOS activity, and thus prevent the production of NO. Inhibitors of NOS have a variety of uses, including but not limited to the treatment of Hypertension, Familial Hyperchloesterolemia, Endothelial Dysfunction, Atherosclerosis, Graft/Transplantation Rejection, Asthma, Neurogenic Airway Edema, Ulcerative Colitis, Colonic Inflammation, Periodontal Disease, Cystic Fibrosis, Vascular Hyporeactivity, Cerebral Ischemia, Migraine, Alzheimer's Disease, and Multiple Sclerosis. Inhibitors of NOS and inhibitors of local inflammation are useful for treating some of the same disorders because inhibitors of NOS also function to inhibit the inflammatory response. Thus, there is some overlap in the list of disorders that are associated with NOS and disorders having an inflammatory component.

The invention also includes methods for preventing and/or treating diseases associated with IL-10. A disease associated with IL-10 is a disease or condition which is treatable by the induction or administration of IL-10. These diseases include at least the same diseases described above as diseases associated with NOS, as well as, the prevention of infection mediated preterm birth. Infection mediated preterm birth is described in Terrone, D. A., et al., *Am. J. Obstet. Gynecol.* 2000, 182(1), which is incorporated by reference.

The compounds are administered in an effective amount for preventing an inflammatory response or for preventing NOS activity. An effective amount for preventing an inflammatory response or for preventing NOS activity as used herein is that amount of an immunomodulating compound of the invention that will, alone or together with further doses or additional therapeutic compounds, inhibit or prevent (as defined above) an inflammatory response or NOS activity, respectively.

The compounds of the invention are also useful for preventing restenosis. Restenosis is a disorder associated with excessive proliferation. In particular arterial restenosis is the expansion of the artery wall due to proliferation of endothelial cells as a result of irritation arising from balloon angioplasty or other treatment. Balloon angioplasty is a widely accepted method of opening blockages in the coronary arteries. The balloon catheter was introduced experimentally in the early 1960's and was first applied clinically in the late 1970's. It has since assumed a major therapeutic role in the treatment of single and multiple vessel coronary artery disease. However in some patients after successful treatment by balloon angioplasty, arterial restenosis occurs, causing reblockage of the artery, not by cholesterol build-up, but by build up of endothelial cells on the inner wall of the artery, thus, reducing the inner diameter (ID) of the artery leading to an infarct. Restenosis may also occur post operatively in for example peripheral vascular systems.

Many methods have been used for treating restenosis including, for example, the methods described in U.S. Pat. Nos. 5,087,244; 5,116,864; 5,092,841; 4,929,602; and 4,820,732; EP 356275; Berk., B. C. et al in the J. Am. Coll. Cardiol. (1991) Vol. 17 #6 Supplement B, pp 111B-117B; PCT Patent Applications WO 9209561; WO 9208472; WO 9207852; WO 9205782 and WO 9118639. The compounds of the invention may be used alone or in combination with the above-disclosed methods or other methods known in the art.

The preparations of the invention when administered "in conjunction with" an inflammatory event and/or surgery, are administered close enough in time with the surgery, trauma or disease that predispose the host to adhesion formation, diseases having an inflammatory component, diseases associated with NOS activity, or sepsis so that a protective effect against the particular disorder is obtained. The preparations may be administered long before the surgery or inflammatory event, e.g., in the case of elective surgery (i.e., weeks or even months) preferably with booster administrations closer in time to (and even after) the surgery or event. Particularly in emergency situations, the preparations may be administered immediately before (minutes to hours) and/or after the inflammatory event or surgery. It is important only that the preparation be administered close enough in time so as to enhance the subject's response against bacterial infection, inflammatory response, adhesion, etc., thereby increasing the chances of a successful host response and reducing the likelihood of sepsis, adhesion formation or development of disease.

The present invention provides pharmaceutical compositions, for medical use, which in some aspects comprise the immunomodulatory compositions of the invention together with one or more pharmaceutically acceptable carriers and optionally other therapeutic ingredients. Thus the invention also relates to immunomodulating pharmaceutical compositions in combination with an anti-infectious agent such as an antibacterial or anti-viral agent, an anti-inflammatory agent, an antibiotic, or other therapeutic agent and a pharmaceutically acceptable carrier. The pharmaceutical compositions useful in the invention may be delivered separately with the other therapeutic or in the form of therapeutic cocktails. A therapeutic cocktail is a mixture of any pharmaceutical composition of the invention and another therapeutic agent. In this embodiment, a common administration vehicle (e.g., tablet, implant, injectable solution, etc.) could contain both the pharmaceutical composition and the other therapeutic agent. Alternatively, the other therapeutic can be separately dosed.

The use of anti-infectious agents, for instance, is routine for the treatment of bacterial, viral and fungal infection. Antibacterial drugs are well known and include but are not limited to: penicillin G, penicillin V, ampicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefinenoxine, ceftriaxone, moxalactam, cefotetan, cefoperazone, ceftazidme, imipenem, clavulanate, timentin, sulbactam, neomycin, erythromycin, metronidazole, chloramphenicol, clindamycin, lincomycin, vancomycin, trimethoprim-sulfamethoxazole, aminoglycosides, quinolones, tetracyclines and rifampin. (See Goodman and Gilman's *Pharmacological Basis of Therapeutics*, 8th Ed., 1993, McGraw Hill, Inc.)

Anti-virals include, for instance, but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime.

Anti-fungals include, for instance, but are not limited to Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofungin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; PyrroInitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; Zinoconazole Hydrochloride.

Anti-inflammatory compounds have been used in the prior art for treating diseases having an inflammatory component. Anti-inflammatory compounds include but are not limited to Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium;

Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Antibiotics are agents which are effective against *Enterobacteriaceae*, such as gentamicin and clindamycin. The antibiotics are preferably used in combination with the prodrug polyanionic polysaccharide gels of this invention.

The precise amounts of the therapeutic agent used in combination with the pharmaceutical compositions of the invention will depend upon a variety of factors, including the pharmaceutical composition selected, the dose and dose-timing selected, the mode of administration, the nature of any surgical or medical procedure contemplated and the characteristics of the subject. Where local administration is carried out, it will be understood that very small amounts may be required (nanograms and possibly picograms). The precise amounts selected can be determined without undue experimentation, particularly since a threshold amount will be any amount which will favorably enhance the immune response. Thus, it is believed that picogram to milligram amounts are possible, depending upon the mode of delivery, but that nanogram to microgram amounts are likely to be most useful.

Multiple doses of the pharmaceutical compositions of the invention are contemplated. For instance, when being administered in conjunction with a surgical procedure the compounds of the invention can be administered in multiple doses over a three week period preceding surgery, over a two week period preceding surgery, over a one week period preceding surgery, over a one day period preceding surgery, etc. Further doses may be administered post surgery as well. Any regimen that prevents an inflammatory response may be used, although optimum doses and dosing regimens are those that would not only inhibit the development of sepsis or adhesion formation or the inflammatory disease, but also would result in a complete protection against sepsis or adhesion formation or the inflammatory disease. Desired time intervals for delivery of multiple doses of a particular pharmaceutical composition can be determined by one of ordinary skill in the art employing no more than routine experimentation.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The pharmaceutical composition may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); succinic acid; and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a pharmaceutical composition optionally included in a pharmaceutically acceptable carrier. The term "pharmaceutically acceptable carrier" means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being commingled with the pharmaceutical compositions of the present invention, and with each other, in a manner such that there is no interaction which would substantially impair the desired pharmaceutical efficiency.

Compositions suitable for parenteral administration conveniently comprise sterile aqueous preparations, which can be isotonic with the blood of the recipient. Among the acceptable vehicles and solvents are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

The pharmaceutical compositions useful in the invention may be delivered in mixtures of more than one pharmaceutical composition. A mixture may consist of several pharmaceutical compositions.

A variety of administration routes are available. The particular mode selected will depend, of course, upon the particular pharmaceutical composition selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration include, e.g., parenteral, injection, infusion, deposition, implantation, anal or vaginal supposition, oral ingestion, inhalation, topical administration. Injections can be e.g., intravenous, intradermal, subcutaneous, intramuscular, or interperitoneal. For example, the pharmaceutical composition can be injected intravenously or intramuscularly for the treatment of sepsis, or can be injected directly into the joints for treatment of arthritic disease, or can be injected directly into the surgical site for prevention of adhesion. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the pharmaceutical composition with an aerosol in an inhaler, either alone or attached to a carrier that can be absorbed. For systemic administration, it may be preferred that the pharmaceutical composition is encapsulated in liposomes. The term "parenteral" includes subcutaneous injections, intravenous, intramuscular, intraperitoneal, intrasternal injection or infusion techniques.

In certain preferred embodiments of the invention, the administration can be designed so as to result in sequential exposure of the pharmaceutical composition over some period of time, e.g., hours, days, weeks, months or years. This can be accomplished by repeated administrations of the pharmaceutical composition, by one of the methods described above, or alternatively, by a sustained-release delivery system in which the pharmaceutical composition is delivered to the subject for a prolonged period without repeated administrations. By sustained-release delivery system, it is meant that total release of the pharmaceutical composition does not occur immediately upon administration, but rather is delayed for some period of time. Release can occur in bursts or it can occur gradually and continuously. Administration of such a system can be, e.g., by long-lasting oral dosage forms, bolus injections, transdermal patches, and subcutaneous implants.

Examples of systems in which release occurs in bursts includes, e.g., systems in which the pharmaceutical composition is entrapped in liposomes which are encapsulated in a polymer matrix, the liposomes being sensitive to specific stimuli, e.g., temperature, pH, light or a degrading enzyme and systems in which the pharmaceutical composition is encapsulated by an ionically-coated microcapsule with a microcapsule core degrading enzyme. Examples of systems in which release of the pharmaceutical composition is gradual and continuous include, e.g., erosional systems in which the pharmaceutical composition is contained in a form within a matrix and effusional systems in which the pharmaceutical composition permeates at a controlled rate, e.g., through a polymer. Such sustained release systems can be e.g., in the form of pellets, or capsules.

In one particular embodiment, the preferred sustained release device is a biocompatible microparticle or microencapsulated product or implant that is suitable for implantation or administration to the mammalian recipient. Exemplary bioerodible implants that are useful in accordance with this method are described in PCT International application no. PCT/US/03307 (Publication No. WO 95/24929, entitled "Polymeric Gene Delivery System". The polymeric matrix preferably is in the form of a microparticle such as a microsphere (wherein the pharmaceutical composition is dispersed throughout a solid polymeric matrix) or a microcapsule (wherein the pharmaceutical composition is stored in the core of a polymeric shell). Other forms of the polymeric matrix for containing the pharmaceutical composition include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used, typically injection into a tissue. The polymeric matrix composition can be selected to have both favorable degradation rates and also to be formed of a material which is bioadhesive, to further increase the effectiveness of transfer when the matrix is administered to a mucosal surface. The matrix composition also can be selected not to degrade, but rather, to release by diffusion over an extended period of time. The biocompatible microsphere may be suitable for oral delivery. Such microspheres are disclosed in Chickering et al., *Biotech. And Bioeng.*, (1996) 52:96-101 and Mathiowitz et al., *Nature*, (1997) 386:.410-414 and PCT Patent Application WO97/03702.

Both non-biodegradable and biodegradable polymeric matrices can be used to deliver the pharmaceutical compositions to the subject. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

Bioadhesive polymers of particular interest include bioerodible hydrogels described by H. S. Sawhney, C. P. Pathak and J. A. Hubell in *Macromolecules*, (1993) 26:581-587, the teachings of which are incorporated herein, casein, gelatin, glutin, polyanhydrides, polyacrylic acid, alginate, chitosan, poly(methyl methacrylates), poly(ethyl methacrylates), poly(butylmethacrylate), polyhyaluronic acids, poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other sustained release delivery systems useful according to the invention include but are not limited to fatty acids and a medicinal pump. Preferably the fatty acids are $C_9$-$C_{20}$ fatty acids.

The compositions may conveniently be presented in unit dosage form and may be prepared by any of the methods well known in the art of pharmacy. All methods include the step of bringing the pharmaceutical composition into association with a carrier which constitutes one or more accessory ingredients. In general, the compositions are prepared by uniformly and intimately bringing the pharmaceutical composition into association with a liquid carrier, a finely divided solid carrier, or both, and then, if necessary, shaping the product. The pharmaceutical composition may be stored lyophilized.

The pharmaceutical compositions can be suspended in a liquid, e.g., in dissolved form or colloidal form. The liquid can be a solvent, partial solvent, or non-solvent. In many cases, water or an organic liquid can be used.

The pharmaceutical compositions are administered to the mammal in a therapeutically-effective amount. By therapeutically-effective amount it is meant that amount which is capable of at least partially preventing, reversing, reducing, decreasing, ameliorating, or otherwise suppressing the inflammatory response being treated. A therapeutically-effective amount can be determined on an individual basis and will be based, at least in part, on consideration of the species of mammal, the mammal's age, sex, size, and health; the type of pharmaceutical composition used, the type of delivery system used; the time of administration relative to the severity of the disease; and whether a single, multiple, or controlled-release dose regimen is employed. A therapeutically-effective amount can be determined by one of ordinary skill in the art employing such factors and using no more than routine experimentation.

In some embodiments, the concentration of the pharmaceutical composition if administered systemically is at a dose of about 1.0 mg to about 2000 mg for an adult of 70 kg body weight, per day. In other embodiments, the dose is about 10 mg to about 1000 mg/70 kg/day. In yet other embodiments, the dose is about 100 mg to about 500 mg/70 kg/day. Preferably, the concentration of the pharmaceutical composition, if applied topically, is about 0.1 mg to about 500 mg/gm of ointment or other base, more preferably about 1.0 mg to about 100 mg/gm of base, and most preferably, about 30 mg to about 70 mg/gm of base. The specific concentration partially depends upon the particular pharmaceutical composition used, as some are more effective than others. The dosage concentration of the pharmaceutical composition actually administered is dependent at least in part upon the particular disorder being treated, the final concentration of pharmaceutical composition that is desired at the site of action, the method of administration, the efficacy of the particular pharmaceutical composition, the longevity of the particular pharmaceutical composition, and the timing of administration relative to the severity of the disease. Preferably, the dosage form is such that it does not substantially deleteriously effect the mammal. The dosage can be determined by one of ordinary skill in the art employing such factors and using no more than routine experimentation.

A "subject" shall mean a human or non-human mammal, including but not limited to, a dog, cat, horse, cow, pig, sheep, goat, chicken, primate, rat, and mouse.

EXAMPLES

Example 1

Preparation of a CMC Formulation 3.53 grams of sodium carboxymethylcellulose (CMC), corrected for moisture by loss-on-drying, was dissolved in 80 ml of SBS (succinate buffered saline), and was let stand at room temperature for 5 minutes. The solution was vortexed at 1500 rpm for 15 minutes. 20 grams of the solution was loaded into syringes and autoclaves. The pH after autoclaving was 4.2. The osmolarity before autoclaving was 369 mos. The syringes were stored for 1 week at 4° C.

Example 2

Preparation of a CMC/10% EDU Autoclaved Formulation 2.38 grams of sodium carboxymethylcellulose, corrected for moisture by loss-on-drying, was dissolved in 80 ml of SBS, and was let stand at room temperature for 5 minutes. The solution was vortexed at 1500 rpm for 15 minutes, and 240 mg of N-ethyl-N'-(3-dimethylaminopropyl) urea (EDU) was added. The material was vortexed and autoclaved. The pH before autoclaving was 4.1, and the osmolarity was 416 mos.

Example 3

Preparation of a CMC/10% EDU Filtered Formulation 2.38 grams of sodium carboxymethylcellulose, corrected for moisture by loss-on-drying, was dissolved in 80 ml of SBS, and was let stand at room temperature for 5 minutes. The solution was vortexed at 1500 rpm for 15 minutes, and 240 mg of EDU in 10 ml SBS buffer which had been sterile filtered was added. The material was vortexed and autoclaved. The pH before autoclaving was 4.4, and the osmolarity was 383.3 mos.

Example 4

Preparation of a Solution of EDU in Succinate Buffer

A 4 mg/ml solution of EDU in SBS buffer was prepared and sterile filtered. The solution was stored at 4° C.

Example 5

Preparation of a CMC/EDC Powder Formulation 52.74 grams of sodium carboxymethylcellulose, corrected for moisture by loss-on-drying, was dissolved in 6.88 kg of water. The solution was chilled to 10° C. and the pH adjusted to 5.5 with 0.1 M HCL. A solution of N-ethyl-N'-(3-dimethylaminopropyl) carbodiimide (EDC) (153.78 grams of EDC to 250 grams of water) was added at an additional rate of 16 grams per minute with vigorous mixing. The pH was maintained for 60 minutes at 5.5 by the addition of 0.1 N HCL. The reaction product was precipitated by consecutively adding a saline solution (250 grams of a solution of 584.4 grams of NaCl in 2 liters of water) in one portion, and ethanol (4 kg, 190 proof) at a rate of 67 grams/minute with vigorous mixing per kilogram of reaction solution. Mixing was stopped and the precipitate was allowed to settle. The supernatant was decanted, and additional ethanol (2 times the mass of the settled precipitate remaining) was added with vigorous mixing. Mixing was stopped again, the powder allowed to settle, and the supernatant was decanted. This washing procedure was repeated one more time.

The precipitated product was collected on a metal screen, washed with additional ethanol, and dried under reduced pressure to a moisture content of less than 10% by weight.

Example 6

Preparation of an HA/EDC Powder Formulation 76.6 grams of hyaluronic acid, corrected for moisture by loss-on-drying, was dissolved in 8.68 kg of water. The solution was cooled to 25° C., and the pH adjusted to 5.5 with 0.1 M HCl. A solution of EDC (96.0 grams of EDC to 235.8 grams of water) was added at a solution rate of 13 grams per minute with vigorous mixing. The pH was maintained for 60 minutes at 5.5 by the addition of 0.1 N HCl. The reaction product was precipitated by adding ethanol (3.5 kg, 190 proof) at a rate of 58 grams/minute with vigorous mixing per kilogram of reaction solution. Mixing was stopped, and the precipitate allowed to settle. The supernatant was decanted, and additional ethanol (2 times the mass of the settled precipitate remaining) was added with vigorous mixing. Mixing was stopped again, the powder allowed to settle, and the supernatant was decanted. This washing procedure was repeated one more time.

The precipitated product was collected on a metal screen, washed with additional ethanol, and dried under reduced pressure to a moisture content of less than 10% by weight.

Example 7

Preparation of an HA-CMC-EDC Powder Formulation 123.44 grams of sodium carboxymethylcellulose and 49.56 grams of hyaluronic acid, corrected for moisture by loss on drying, was dissolved in 8.51 kg of water. The solution was cooled to 25° C., and the pH adjusted to 5.5 with 0.1 N HCL. A solution of EDC (96.0 grams of EDC to 235.8 grams of water) was added at an additional rate of 13 grams per minute with vigorous mixing. The pH was maintained for 60 minutes at 5.5 by the addition of 0.1 N HCL. The reaction product was precipitated by adding ethanol (3.5 kg, 190 proof) at a rate of 60 grams/minute with vigorous mixing per kilogram of reaction solution. Mixing was stopped, and the precipitate was allowed to settle. The supernatant was decanted, and additional ethanol (2 times the mass of the settled precipitate remaining) was added with vigorous mixing. Mixing was stopped again, the powder allowed to settle, and the supernatant was decanted. This washing procedure was repeated one more time.

The precipitated product was collected on a metal screen, washed with additional ethanol, and dried under reduced pressure to a moisture content of less than 10% by weight. The powder was then heated at 100° C. for a minimum of 45 minutes.

Example 8

Animal Model and Procedure Used to Stimulate Human Intraabdominal Infections Associate with Sepsis and for Assessment of the Effectiveness of Drug Administration The model system utilizes Wistar rats surgically implanted with an inoculum of intestinal contents from other rats. The inoculum is prepared in a manner which simulates the microbiologic parameters of the human colon. This is accomplished by placing rats on a diet of lean ground beef for two weeks, and then harvesting, homogenizing and freezing aliquots of prepared intestinal contents for subsequent use. The clinical end points for evaluation in this model are mortality, while microbiologic end points include blood and peritoneal cultures. The general experimental design and methods are as follows.

Male, Wistar, virus antibody free (VAF) rats (Charles River Laboratories, Wilmington, Mass.), weighing 175-200 grams, are utilized for all experiments. All animals are housed, five per cage, within a VAF facility, and given food and water ad libitum, except for those animals used for preparation of the meat-fed cecal inoculum (see below). Animal experiments are carried out according to the guidelines of the Harvard Medical Area Standing Committee on Animals, in facilities accredited by the American Association for the Accreditation of Laboratory Animal Care.

The innoculum for this study is prepared as described in A. Onderdonk et al., *Experimental intra-abdominal abscesses in rats; quantitative bacteriology of infected animals*. Infection and Immunity, 10:1256-9 (1974); and A. Onderdonk et al., *Experimental intra-abdominal abscesses in rats: development of animal model*. Infection and Immunity, 10:1256-1259 (1974). Briefly, cecal contents from meat-fed rats are combined with peptone-yeast-glucose broth to form a slurry. This slurry is filtered through gauze to remove large particulate material, aliquoted and frozen at −80° C. until used. Preliminary testing of this inoculum is performed to determine the proper dilution of the inoculum to yield a mortality of 60%-70% in an untreated group.

Animals are anesthetized with Nembutal (50 mg/Kg), and prepared for surgical implantation of the inoculum by shaving the abdomen and applying an iodine solution. A 3-4 cm midline incision is made through the skin and anterior abdominal wall, and a gelatin capsule containing 0.5 mL of the inoculum is inserted into the pelvic region. The incision is closed with one 3-0 suture, and the animals are observed four times per day for the first 48 hours, and every eight hours thereafter. Visibly moribund animals are humanely sacrificed with $CO_2$.

Groups of twenty animals each are implanted with the inoculum described above. For each experiment, a control group of sham-treated animals is employed. For experiments in which quantitative blood and peritoneal cultures are obtained, sufficient additional animals are implanted to allow for such cultures, but mortality in these groups is not included in the clinical outcome calculations, due to the additional manipulation of the animals. Surviving animals from each group are sacrificed after seven days.

At various times post surgery, 5 animals in each group are anesthetized, and a 0.1 ml sample of peritoneal fluid obtained by a 0.5 cm midline incision. At the same time, 0.1 ml of blood is obtained by the percutaneous, transthoracic route. Each sample is serially diluted in sterile saline, and aliquots plated onto appropriate media (BMB and LKV for obligate anaerobes; TSA, MAC and chocolate agar for facultative species). Following incubation at 37° C. in the appropriate atmosphere for 48 hours, colonies are enumerated, and the major isolates identified by standard methods. All colony counts are expressed as log CFR/ml of sample.

A comparison of groups with regard to mortality is made by chi-square analysis as supplied on commercially available statistical software (Instat, GraphPad Software, San Diego, Calif.). A comparison group mean bacterial count is made using Student's T test.

The following Examples illustrate the use of the compositions of this invention to treat intraabdominal sepsis, infection, and surgical adhesions using various forms of the above-described procedures.

Example 9

Animals were divided into Groups A, B, C, D, E, F and G, with each Group containing 10 animals. All groups were challenged with $5 \times 10^7$ cfu *Escherichia coli*, mixed 1:1 with Sterile Cecal Contents, and were treated 25 hours before challenge with 0.5 ml of material by intramuscular injection. Group A was treated with saline. Group B was treated with EDU in succinate buffer (4 g/ml). Group C was treated with a 4% CMC solution. Group D was treated with CMC/10% EDU which had been autoclaved. Group E was treated with CMC/10% EDU which had been filtered. Group F was treated with a 4% CMC/EDC gel. Group G was treated with a 5% HA/CMC gel.

The animals were held for 48-72 hours, and assessed for mortality vs. the saline control.

The results are shown in Table 1, where the designation "A" indicates surviving animals, and "M" indicates mortalities:

TABLE 1

| | Group | | | | | | | | | | | | |
|---|---|---|---|---|---|---|---|---|---|---|---|---|---|
| | A | | B | | C | | D | | E | | F | | G |
| | A | M | A | M | A | M | A | M | A | M | A | M | A | M |
| Post Op | 10 | | 10 | | 10 | | 10 | | 10 | | 10 | | 10 | |
| 24 hr | 7 | 3 | 8 | 2 | 9 | 1 | 10 | 0 | 9 | 1 | 9 | 1 | 9 | 1 |
| 48 | 6 | 1 | 8 | 0 | 8 | 1 | 9 | 1 | 9 | 0 | 9 | 0 | 9 | 0 |
| Total | 6 | 4 | 8 | 2 | 8 | 2 | 9 | 1 | | 1 | 9 | 1 | 9 | 1 |
| % Total M | 40% | | 20% | | 20% | | 10% | | 10% | | 10% | | 10% | |

Example 10

Animals were divided into Groups A, B, C, D and E, with each Group containing 20 animals. All groups were challenged with *Escherichia coli*, mixed 1:1 with Sterile Cecal Contents, and were treated with saline. Group B was treated with EDU in succinate buffer (4 mg/ml). Group C was treated with CMC/10% EDU which had been filtered. Group B was treated with a 4% CMC/EDC gel. Group E was treated with a 5% HA/CMC gel. The animals were held for 48-72 hours, and assessed for mortality vs. the saline control.

The results are shown in Table 2, where the designation "A" indicates surviving animals, and "M" indicates mortalities:

TABLE 2

| | Group | | | | | | | | | |
|---|---|---|---|---|---|---|---|---|---|---|
| | A | | B | | C | | D | | E | |
| | A | M | A | M | A | M | A | M | A | M |
| Post Op | 20 | | 20 | | 20 | | 19 | | 20 | |
| 24 hr | 8 | 12 | 18 | 2 | 13 | 7 | 17 | 2 | 16 | 4 |
| 48 hr | 8 | 0 | 16 | 2 | 11 | 2 | 14 | 3 | 15 | 1 |
| Total | 8 | 12 | 16 | 4 | 11 | 9 | 14 | 5 | 15 | 5 |
| % Total M | 60% | | 20% | | 45% | | 26.3% | | 25% | |

Example 11

Animals were divided into Groups A, B, C, D and E, with each Group containing 10 animals. All groups were challenged with $5 \times 10^7$ cfu *Escherichia coli*, mixed 1:1 with Sterile Cecal contents and were treated 24 hours before challenge with 0.5 ml of material by intramuscular injection. Group A was treated with saline. Group B was treated with succinate buffer. Group C was treated with EDU in succinate buffer. Group D was treated with EDU in a saline solution. Group E was treated with EDU: in PBS buffer.

The animals were held for 48-72 hours, and assessed for mortality vs. the saline control.

The results are shown in Table 3, where the designation "A" indicates surviving animals, and "M" indicates mortalities:

TABLE 3

| | Group | | | | | | | | | |
|---|---|---|---|---|---|---|---|---|---|---|
| | A | | B | | C | | D | | E | |
| | A | M | A | M | A | M | A | M | A | M |
| Post Op | 4 | 6 | 4 | 6 | 9 | 1 | 7 | 2 | 4 | 6 |
| 48 hrs | 4 | 0 | 4 | 0 | 9 | 0 | 7 | 0 | 4 | 0 |
| % Total M | 60% | | 60% | | 10% | | 22.2% | | 60% | |

Example 12

Animals were divided into Groups A, B, and C, with each Group containing 10 animals. All groups were challenged with 0.706 ml *Escherichia coli*, 2.125 ml Sterile Cecal Contents, and 14.169 ml Peptone Yeast Glucose. Groups A and B were treated immediately after challenge with about 2 ml of the material placed over the exposed intestines, and the incision was closed with sutures as per SOP. Group C was treated 24 hours before challenge. Group A was treated with 2 ml saline; and Groups B and C were treated with a 2.0 ml HA/CMC/EDC gel.

The animals were held for 48-72 hours, and assessed for mortality vs. the saline control.

The results are shown in Table 4, where the designation "A" indicates surviving animals, and "M" indicates mortalities:

TABLE 4

| | Group | | | | | | | | |
|---|---|---|---|---|---|---|---|---|---|
| | A | | | B | | | C | | |
| | A | M | % | A | M | % | A | M | % |
| Post Op | 9 | | | 10 | | | 9 | | |
| 24 hr | 2 | 7 | 78 | 0 | 10 | 100 | 8 | 1 | 11 |
| 48 hr | 2 | 0 | 78 | 0 | 10 | 100 | 8 | 1 | 11 |
| Total | 2 | 7 | 78 | 0 | 10 | 100 | 8 | 1 | 11 |

Example 13

Animals were divided into Groups A, B, C, D, E and F, with each Group containing 20 animals. All groups were challenged with 2.500 ml *Escherichia coli*, 5.500 ml Sterile Cecal Contents, and 57.98 ml Peptone Yeast Glucose. Groups A, C, D and E were treated immediately after challenge with about 2 ml of the material placed over the exposed intestines, and the incision was closed with sutures as per SOP. Group B was treated after challenge by placing a 2.5 cm² piece of material over the exposed intestines and closing the incision with sutures as per SOP. Group A was treated with 2 ml saline; Group B was treated with an Interceed™-TC7 absorbable adhesion barrier; Groups C, D and E were treated with a 2.5% CMC/EDC gel; Group F was injected with 2 ml of an HA/CMC/EDC gel 24 hours before challenge.

The animals were held for 48-72 hours, and assessed for mortality vs. the saline control.

The results are shown in Table 5.

TABLE 5

| | Group A | | | Group B | | | Group C | | | Group D | | | Group E | | | Group F | | |
|---|---|---|---|---|---|---|---|---|---|---|---|---|---|---|---|---|---|---|
| | A | M | % | A | M | % | A | M | % | A | M | % | A | M | % | A | M | % |
| Post Op | 19 | | | 19 | | | 19 | | | 19 | | | 19 | | | 19 | 1 | |
| 24 hr | 5 | 14 | 74 | 6 | 13 | 68 | 5 | 14 | 74 | 1 | 18 | 95 | 3 | 16 | 84 | 16 | 2 | 11 |
| 48 | 5 | 0 | 74 | 5 | 1 | 74 | 4 | 1 | 79 | 0 | 1 | 100 | 3 | 0 | 84 | 16 | 0 | 11 |
| Total | 5 | 14 | 74 | 5 | 14 | 74 | 4 | 15 | 79 | 0 | 19 | 100 | 3 | 16 | 84 | 16 | 2 | 11 |

Example 14

Animals were divided into Groups A and B, with each Group containing 10 animals. All groups were challenged with 0.417 ml *Escherichia coli*, 0.917 ml Sterile Cecal Contents, and 9.660 ml Peptone Yeast Glucose. Groups A and B were treated 24 hours before challenge. Group A was treated with 2 ml of saline I.M., and Group B was treated with 2 ml of a 2.0 ml HA/CMC/EDC gel I.M.

The animals were held for 48-72 hours, and assessed for mortality vs. the saline control.

The results are shown in Table 6.

TABLE 6

| | Group A | | | Group B | | |
|---|---|---|---|---|---|---|
| | A | M | % | A | M | % |
| Post Op | 10 | | | 10 | | |
| 24 hr | 7 | 3 | 30 | 10 | 0 | 0 |
| 48 hr | 6 | 1 | 40 | 10 | 0 | 0 |
| Total | 6 | 4 | 40 | 10 | 0 | 0 |

Example 15

Animals were divided into Groups A, B, C and D, with each Group containing 15 animals. All groups were challenged with 2.629 ml gentamicin resistant *Escherichia coli*, 0.32 ml Dextran Sulfate, and 29.051 ml Peptone Yeast Glucose. Group A was treated 2 hours after challenge, while Groups B and C were treated 24 hours before challenge. Group A was treated with 2 ml saline I.M.; Group B was treated with 2 mg Gentamicin; Group C was treated with 2 ml HA/CMC/EDC gel I.M.; and Group D was treated with a mixture of Gentamicin and HA/CMC/EDC gel.

The animals were held for 48 hours, and assessed for mortality vs. the saline control.

The results are shown in Table 7.

TABLE 7

| | Group A | | | Group B | | | Group C | | | Group D | | |
|---|---|---|---|---|---|---|---|---|---|---|---|---|
| | A | M | % | A | M | % | A | M | % | A | M | % |
| Post Op | 14 | | | 13 | | | 14 | | | 14 | | |
| 24 hr | 6 | 8 | 57.1 | 10 | 3 | 23.1 | 14 | 0 | 0 | 13 | 1 | 7.1 |
| 48 hr | 3 | 3 | 78.6 | 8 | 2 | 38.5 | 14 | 0 | 0 | 12 | 1 | 14.3 |
| Total | 3 | 11 | 78.6 | 8 | 5 | 38.5 | 14 | 0 | 0 | 12 | 2 | 14.3 |

Example 16

Animals were divided into Groups A, B, C, D, E and F, with each Group containing 10 animals. All groups were challenged with 1.396 ml *Escherichia coli*, 2.66 ml Sterile Cecal Contents, and 27.937 ml Peptone Yeast Glucose. All Groups were treated 24 hours before challenge I.M. Group A was treated with 0.5 ml saline; Group B was treated with 2 ml HA/CMC/EDC gel; Group C was treated with 1 ml HA/CMC/EDC gel; Group D was treated with 0.5 ml HA/CMC/EDC gel; Group E was treated with 0.1 ml HA/CMC/EDC gel; and Group F was treated with 0.05 ml HA/CMC/EDC gel.

The animals were held for 48-72 hours, and assessed for mortality vs. the saline control.

The results are shown in Table 8.

TABLE 8

| | Group A | | | Group B | | | Group C | | | Group D | | | Group E | | | Group F | | |
|---|---|---|---|---|---|---|---|---|---|---|---|---|---|---|---|---|---|---|
| | A | M | % | A | M | % | A | M | % | A | M | % | A | M | % | A | M | % |
| Post op | 9 | | | 10 | | | 9 | | | 10 | | | 10 | | | 10 | | |
| 24 hr | 2 | 7 | 78 | 6 | 4 | 40 | 8 | 1 | 11 | 7 | 3 | 30 | 2 | 8 | 80 | 2 | 8 | 80 |

TABLE 8-continued

| | Group | | | | | | | | | | | | | | | | | |
|---|---|---|---|---|---|---|---|---|---|---|---|---|---|---|---|---|---|---|
| | A | | | B | | | C | | | D | | | E | | | F | | |
| | A | M | % | A | M | % | A | M | % | A | M | % | A | M | % | A | M | % |
| 48 hr | 2 | 0 | 78 | 6 | 0 | 40 | 8 | 0 | 11 | 7 | 0 | 30 | 2 | 0 | 80 | 2 | 0 | 80 |
| Total | 2 | 7 | 78 | 6 | 4 | 40 | 8 | 1 | 11 | 7 | 3 | 30 | 2 | 8 | 80 | 2 | 8 | 80 |

Example 17

Animals were divided into Groups A, B. C and D, with each Group containing 20 animals. All groups were challenged with 1.960 ml resistant *Escherichia coli,* 375 ml Sterile Cecal Contents, and 39.290 ml Peptone Yeast Glucose. All Groups were treated with 0.5 ml of material injected I.M. 24 hours prior to challenge. Group A was treated with saline; Groups B and C were treated with 2.5% w/w CMC/EDC gel; and Group D was treated with 4.0% w/w HA/EDC gel.

The animals were held for 48 hours, and assessed for mortality vs. the saline control.

The results are shown in Table 9.

TABLE 9

| | Group | | | | | | | | | | | |
|---|---|---|---|---|---|---|---|---|---|---|---|---|
| | A | | | B | | | C | | | D | | |
| | A | M | % | A | M | % | A | M | % | A | M | % |
| Post Op | 20 | | | 19 | | | 19 | | | 20 | | |
| 24 hr | 14 | 6 | 30 | 18 | 1 | 5.3 | 17 | 2 | 10.5 | 17 | 3 | 15 |
| 32 hr | 13 | 1 | 35 | 18 | 0 | 5.3 | 16 | 1 | 15.8 | 16 | 1 | 20 |
| 48 hr | 13 | 0 | 35 | 18 | 0 | 5.3 | 16 | 0 | 15.8 | 16 | 0 | 20 |
| Total | 13 | 7 | 35 | 18 | 1 | 5.3 | 16 | 3 | 15.8 | 16 | 4 | 20 |

Example 18

Animals were divided into Groups A, B, C, D, and E, with Groups A, B and C containing 20 animals, and Groups D and E containing 10 animals. All groups were challenged with) 0.570 ml *Escherichia coli,* 4.500 ml Sterile Cecal Contents, and 39.930 ml Peptone Yeast Glucose. Groups A, B and C were treated with 2 ml of material immediately after challenge; and Groups D and E were treated with 0.5 ml of material I.M. 24 hours prior to challenge. Group A was treated with saline; Group B was treated with 4% w/w CMC/EDC gel with no DHT; Group C was treated with 4% w/w CMC/EDC gel with DHT; Group D was treated with 3% w/w HA/APL gel; and Group E was treated with 2.5% CMC/EDC gel.

The animals were held for 48 hours, and assessed for mortality vs. the saline control.

The results are shown in Table 10.

TABLE 10

| | Group | | | | | | | | | | | | | | |
|---|---|---|---|---|---|---|---|---|---|---|---|---|---|---|---|
| | A | | | B | | | C | | | D | | | E | | |
| | A | M | % | A | M | % | A | M | % | A | M | % | A | M | % |
| Post Op | 19 | | | 19 | | | 19 | | | 10 | | | 10 | | |
| 24 hr | 16 | 3 | 15.8 | 17 | 2 | 10.5 | 13 | 6 | 31.6 | 8 | 2 | 20 | 9 | 1 | 10 |
| 48 hr | 16 | 0 | 15.8 | 17 | 0 | 10.5 | 13 | 0 | 31.6 | 8 | 0 | 20 | 9 | 0 | 10 |
| Total | 16 | 3 | 15.8 | 17 | 2 | 10.5 | 13 | 6 | 31.6 | 8 | 2 | 20 | 9 | 1 | 10 |

Example 19

Assessment of the Effect of Sustained Release of EDU on Sepsis Formation

In order to determine whether EDU administered in a time release fashion inhibits mortality in an animal model of intra-abdominal sepsis. EDU was delivered through a micro-osmotic pump to a rat model of sepsis. An Alzet™, Model 1007D micro-osmotic pump was used to deliver 4 milligrams per 7 day period of EDU to male Wistar rats (0.5 μl per hour). After 48 hours, the animals were anesthetized (Nembutal, 0.2 ml of 50 mg/ML solution 1M). The posterior scapulae area of the animal was shaved and prepped with betadine solution and a small incision was made in the skin. Using hemostatis, a small pocket was formed by spreading apart the subcutaneous connective tissues. A solution of EDU, 10 mg in 100 μl of succinate buffer was placed in the osmotic chamber and placed in the pocket described above. The skin incision was closed with 3-0 silk sutures. At time zero the animals were challenged with a $ID_{50}$ mixed microbial innoculum. The animals were then assessed for mortality over time. The results of the study are shown in FIG. 1.

Example 20

Assessment of the Effect of Sustained Release of EDU on Adhesion Formation

In order to determine whether EDU administered in a time release fashion will inhibit adhesion formation in the Cecal Abrasion Model, EDU was delivered using an osmotic pump.

Animals: ♂ Wistar Rats, 175-200 gms.

Osmotic pump: Alzet™ model 1003D Micro-osmotic pump. 1.0 µl/hr.

At time zero, animals were anesthetized (Nembutal, 0.2 mL or 50 mg/mL solution IM). The posterior scapulac area of the animal was shaved and prepped with betadine solution, followed by a small incision which was made in the skin and using hemostats, a small pocket was formed by spreading apart the subcutaneous connective tissues. A solution of EDU, 10 mg in 100 µl of succinate buffer was placed in the osmotic chamber and placed in the pocket described above, this represents a dosage of 2.4 mg/day at a rate of 0.1 mg/hr. The skin incision was closed with 3-0 silk sutures.

Figure 2:
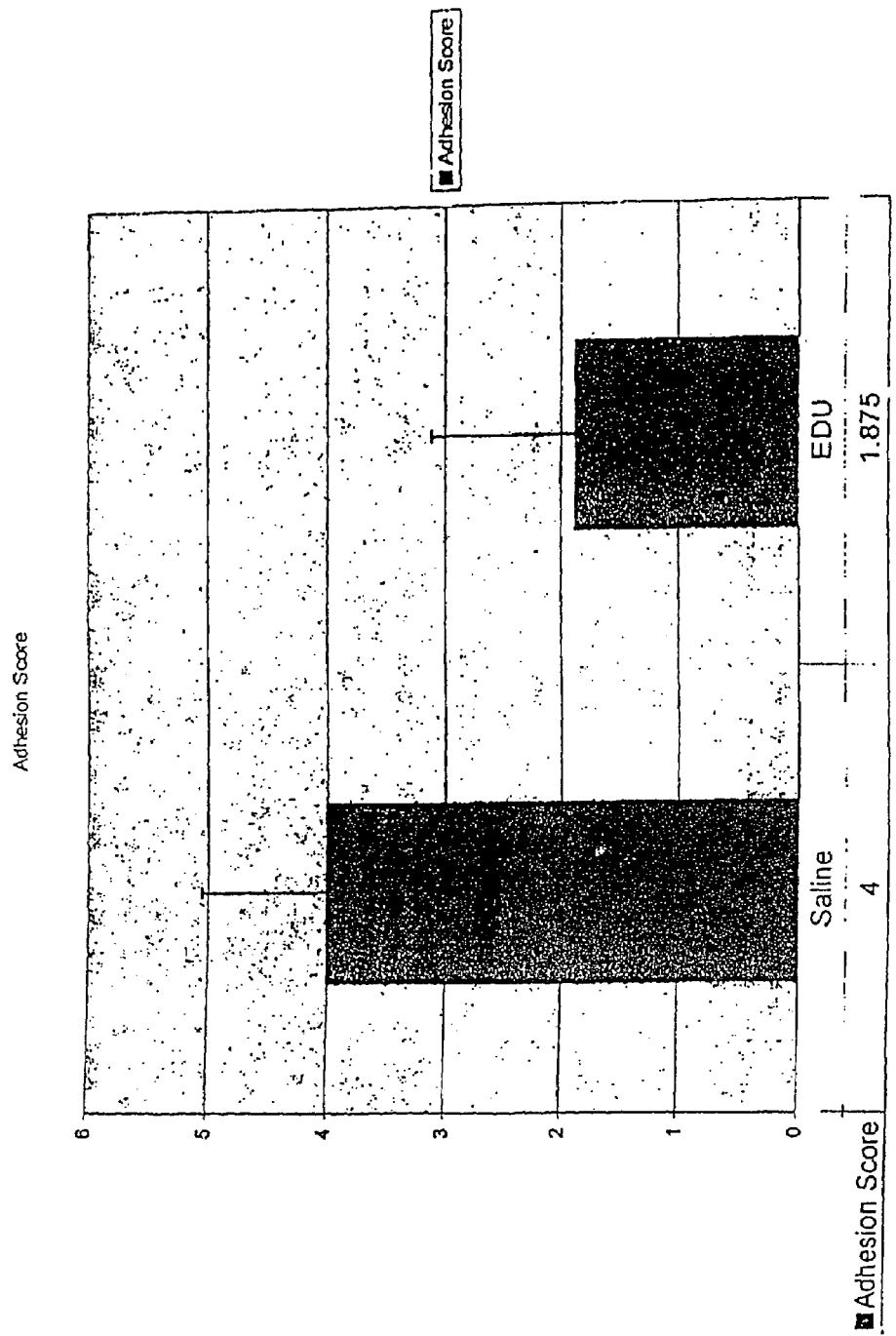
FIG. 2 is a bar graph depicting the effect of EDU on adhesion in a rat model of surgical adhesion.
Figure 3:
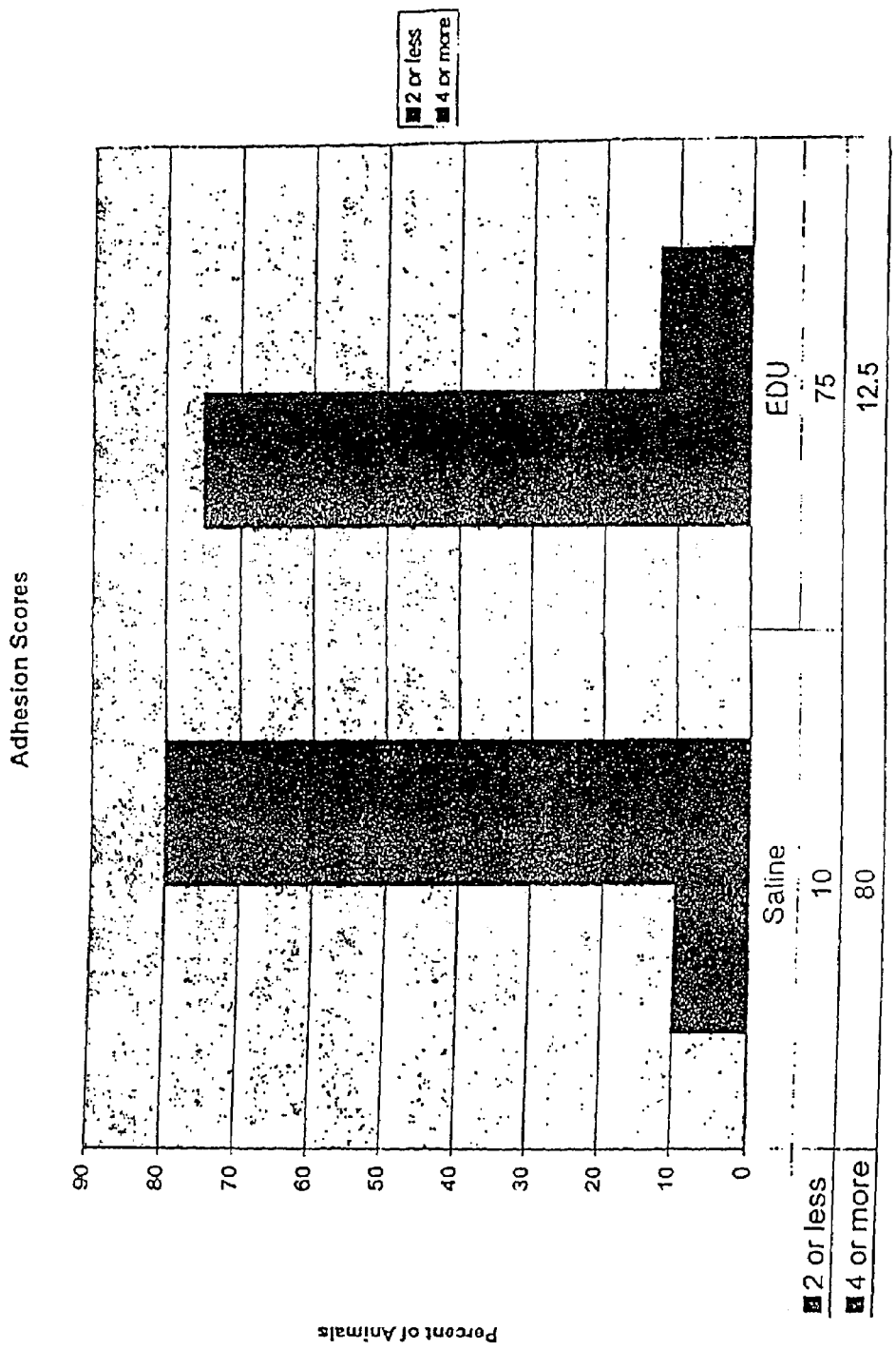
FIG. 3 is a bar graph depicting the effect of EDU on adhesion in a rat model of surgical adhesion.

Twenty four hours later adhesions were induced by scrubbing the cecum and opposing abdominal wall with surgical gauze followed by the addition of SCC. Animals were sacrificed six days later and scored for severity of surgical adhesions as previously described (Kennedy et al., Surgery, 120, 5, p.866-869 (1996). The data is shown in FIGS. 2 and 3 as well as Table 11 set forth below. Group A consisted of 10 animals treated at time zero with saline. Group B consisted of 10 animals treated at time zero with 10 mg of EDU.

An Adhesion Index was used to characterize the adhesions that developed in the animals. This Index included the following parameters:
 0 no adhesions
 1 thin filmy adhesions
 2 more than one thin adhesion
 3 thick adhesion with focal point
 4 thick adhesion with planar attachment
 5 very thick vascularized adhesions or more than one planar adhesion

TABLE 11

| Parameter: | Saline | EDU |
|---|---|---|
| Mean: | 4.000 | 1.875 |
| # of points: | 10 | 8 |
| Std. deviation: | 1.054 | 1.246 |

The data is shown in FIGS. 2 and 3. FIG. 2 is a bar graph depicting the adhesion quantified as an Adhesion Score in animals treated with EDU or a saline control. Treatment of the animals with EDU caused a drop in adhesion score from 4 to 1.875. FIG. 3 is a bar graph depicting the effect of EDU on adhesion in a rat model of surgical adhesion. The number of adhesions in animals treated with EDU was significantly less than the number of animals treated with saline alone.

Example 21

Animals were divided into two groups. Both groups were challenged with *Escherichia coli*, mixed 1:1 with Sterile Cecal Contents. The first group was treated with saline and the second group was treated with a 5% HA/CMC gel. The animals were held for 48-72 hours, and assessed for induction of IL-10. The results are shown in FIG. 4. At 4 hours there was a rapid induction of IL-10 in the HA/CMC gel group but only a minimal induction in the saline control group.

Example 22

Diimide Modified HA and CMC gel (HA/CMC) was evaluated for its ability to reduce adhesions in a rat cecal abrasion model. HA/CMC gel was administered by intramuscular injection at times prior to, during and after surgical abrasion.

Animal: Female Sprague Dawley Rats, 200-350 g

HA/CMC Gel: A gel prepared by reacting 1-ethyl-3-(3-dimethylaminepropyl) carbodiimide, hydrochloride with solutions of hyaluronic acid and/or sodum carboxymethyl cellulose. Gels were prepared from this product by resuspending in succiniate buffered saline, pH 4.0 at a concentration of 5% w/w followed by steam sterilization.

Animals were administered either 0.5 mL intramuscularly of HA/CMC Gel (Group B, N=19) or sterile saline (Groups A, N=20) at −24, −12, 0, and +24 hours relative to the surgical abrasion. Each animal was anesthetized with a single injection of ketamine hydrochloride (85 mg/kg) and xylazine hydrochloride (6 mg/kg), administered into the large muscles of the thigh. A bland ophthalmic ointment was placed in each eye to protect it from corneal desiccation and ulceration. The rat was placed in dorsal recumbency on a water circulating heating pad and covered with a sterile fenestrated drape. A skin incision was initiated about 3 cm below the xyphoid process and continued caudally approximately 2 cm with a #10 scalpel blade. The abdominal muscle was tented with forceps and incised with a #11 scalpel. The midline muscle incision was continued with iris scissors and the cecum was externalized. The cecum was abraded on four sites (2 on the ventral surface, 2 on the dorsal surface) with a mechanical abrading device that permits operator independent, controlled abrasion over a defined area. The cecum was returned to the abdominal cavity. The incisions of all animals was closed in two layers: the muscle and peritoneum was closed in a simple continuous pattern with 3-0 polypropylene suturing material, while the skin and attending fascia was closed with 9 mm stainless steel staples. Animals was allowed to recover completely in an incubator. After seven days, all the animals were euthanized via $CO_2$ asphyxiation and scored blinded for adhesion formation on a 0 to 4 scale.

0 = no adhesions
 1 = filmy adhesions with easily identifiable plane
 2 = mild adhesions with freely dissectable plane
 3 = moderate adhesions with difficult dissection of plane
 4 = dense adhesions with non-dissectable plane The number of animals in each group with at least one significant (grade 2 or higher) adhesion, as well as the number of animals in each group with no adhesions, were compared with the negative control. The results are shown in Table 12 and show that the average incidence and precentage of animals with severe adhesions will be accepted as statistically significant.

TABLE 12

| | % Animals with ≧ Grade 2 | Average Incidence | % Animals with No Adhesions |
|---|---|---|---|
| Control (N = 19) | 68 | 1.3 | 26 |
| HA/CMC Treated (N = 20) | 50 | 0.75 | 45 |

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

What is claimed is:

1. A method for treating arthritis, comprising administering to a subject with arthritis an effective amount of a pharmaceutical composition, said pharmaceutical composition comprising

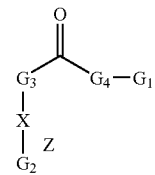

N-ethyl-N'-(3-dimethylaminopropyl)urea or a salt thereof.

* * * * *

UNITED STATES PATENT AND TRADEMARK OFFICE
CERTIFICATE OF CORRECTION

PATENT NO.        : 7,456,220 B2
APPLICATION NO. : 11/176701
DATED             : November 25, 2008
INVENTOR(S)      : Pericles Calias et al.

Page 1 of 1

It is certified that error appears in the above-identified patent and that said Letters Patent is hereby corrected as shown below:

Claim 1

Col. 38, Line 1-10, delete the following structural formula:

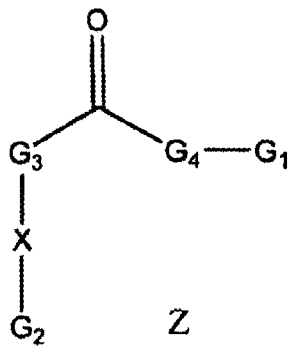

Signed and Sealed this

Twenty-fourth Day of February, 2009

JOHN DOLL
*Acting Director of the United States Patent and Trademark Office*